US012779154B2

(12) United States Patent
Hartono

(10) Patent No.: US 12,779,154 B2
(45) Date of Patent: Nov. 3, 2026

(54) ANCHOR FOR A PATIENT INTERFACE

(71) Applicant: ResMed Asia Pte. Ltd., Singapore (SG)

(72) Inventor: Marvin Sugi Hartono, Singapore (SG)

(73) Assignee: ResMed Asia Pte. Ltd., Singapore (SG)

( * ) Notice: Subject to any disclaimer, the term of this patent is extended or adjusted under 35 U.S.C. 154(b) by 793 days.

(21) Appl. No.: 18/169,547

(22) Filed: Feb. 15, 2023

(65) Prior Publication Data

US 2023/0256181 A1 Aug. 17, 2023

(30) Foreign Application Priority Data

Feb. 15, 2022 (SG) .......................... 10202201454R

(51) Int. Cl.
*A61M 16/00* (2006.01)
*A61M 16/06* (2006.01)
*A61M 16/16* (2006.01)

(52) U.S. Cl.
CPC .... *A61M 16/0066* (2013.01); *A61M 16/0003* (2014.02); *A61M 16/022* (2017.08); *A61M 16/0688* (2014.02); *A61M 16/16* (2013.01)

(58) Field of Classification Search
CPC .......... A61M 16/0683; A61M 16/0066; A61M 16/0003; A61M 16/022
See application file for complete search history.

(56) References Cited

U.S. PATENT DOCUMENTS

| | | | | |
|---|---|---|---|---|
| 4,782,832 A | 11/1988 | Trimble et al. | | |
| 7,478,635 B2 * | 1/2009 | Wixey | A61M 16/021 | 128/204.23 |
| 8,453,640 B2 | 6/2013 | Martin et al. | | |
| 9,010,324 B2 | 4/2015 | Martin et al. | | |
| 10,307,560 B2 | 6/2019 | Martin et al. | | |
| 10,874,820 B2 | 12/2020 | Martin et al. | | |
| 2009/0044808 A1 | 2/2009 | Guney et al. | | |
| 2010/0000534 A1 | 1/2010 | Kooij et al. | | |
| 2015/0296550 A1 * | 10/2015 | Shelly | A61M 16/06 | 320/108 |
| 2017/0119988 A1 * | 5/2017 | Allan | A61M 16/0683 | |
| 2018/0147374 A1 * | 5/2018 | Salmon | A61M 16/0003 | |
| 2018/0272086 A1 * | 9/2018 | Klinger | A61M 5/1415 | |
| 2021/0060284 A1 | 3/2021 | Martin et al. | | |
| 2021/0205553 A1 * | 7/2021 | Salmon | A61M 16/0875 | |

(Continued)

FOREIGN PATENT DOCUMENTS

| | | |
|---|---|---|
| WO | WO 98/004310 A1 | 2/1998 |
| WO | WO 2004/073778 A1 | 9/2004 |
| WO | WO 2005/063328 A1 | 7/2005 |

(Continued)

OTHER PUBLICATIONS

"*Respiratory Physiology*", by John B. West, Lippincott Williams & Wilkins, 9th edition published 2012 (8 pages).

*Primary Examiner* — Joseph D. Boecker
*Assistant Examiner* — Jaeick Jang
(74) *Attorney, Agent, or Firm* — Nixon & Vanderhye P.C.

(57) ABSTRACT

An apparatus for providing positive pressure respiratory therapy to a patient breathing in a respiratory cycle includes an anchor on a housing configured to secure a patient interface to the apparatus when not in use by the patient.

22 Claims, 11 Drawing Sheets

(56) References Cited

U.S. PATENT DOCUMENTS

2022/0126046 A1* 4/2022 King ................. A61M 16/0003

FOREIGN PATENT DOCUMENTS

| | | | |
|---|---|---|---|
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |

* cited by examiner

ANCHOR FOR A PATIENT INTERFACE

1 CROSS-REFERENCE TO RELATED APPLICATIONS

This application claims priority to Singaporean Patent Application No. 10202201454R, filed Feb. 15, 2022, the entire contents of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g., apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$. For flow therapies such as nasal HFT, the patient interface is configured to insufflate the nares but specifically to avoid a complete seal. One example of such a patient interface is a nasal cannula.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g., filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask, and this may impact on patient compliance.

As the patient interface is commonly used during sleep, there is also a problem of the patient interface being misplaced or crushed by a user's body weight. There is also a need for a patient interface which can operate interactively (to some extent) and autonomously with the controller, RPT device, data management system, screening, diagnosis and monitoring system, a smart device or the likes.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g., by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g., because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g., for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus, a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus, RPT devices may also act as flow therapy devices. Examples of RPT devices include a CPAP device and a ventilator.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

2.2.3.5 Data Management

There may be clinical reasons to obtain data to determine whether the patient prescribed with respiratory therapy has been "compliant", e.g., that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular, it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

An aspect of the present technology relates to an apparatus for providing positive pressure respiratory therapy to a patient breathing in a respiratory cycle including an inhalation portion and an exhalation portion, comprising: a controllable motor-blower configured to generate a supply of air at a positive pressure relative to ambient pressure by rotating an impeller at an impeller speed; a housing holding said motor-blower, the housing comprising an inlet and a connection port, the connection port being structured to communicate said supply air at said positive pressure from the motor-blower to a patient interface via an air circuit in use; a sensor configured to monitor at least one of pressure and a flow rate of the supply of air at positive pressure and to generate a sensor output; a controller configured to adjust an operating parameter of said motor-blower in accordance with said sensor output to maintain a minimum positive pressure in said patient interface (e.g., during a treatment session by causing an increase in the impeller speed during the inhalation portion of the respiratory cycle and causing a decrease in the impeller speed during the exhalation portion of the breathing cycle); and an anchor on the housing adapted to secure the patient interface to the apparatus when not in use by the patient.

One form of the present technology comprises an apparatus for providing positive pressure respiratory therapy to a patient breathing in a respiratory cycle including an inhalation portion and an exhalation portion, comprising a controllable motor-blower configured to generate a supply of air at a positive pressure relative to ambient pressure by rotating an impeller at an impeller speed, a housing holding said motor-blower, wherein the housing comprises an anchor configured to secure a patient interface to the apparatus.

Another aspect of one form of the present technology is the anchor is magnetic.

Another aspect of one form of the present technology is the anchor comprises a connector for electrically communication between the patient interface and the apparatus.

Another aspect of one form of the present technology is the anchor is positioned so as to not hinder a user from removing a humidifier of the apparatus.

Another aspect of one form of the present technology is the anchor includes a charger.

Another aspect of one form of the present technology is apparatus is configured to cut power to the controllable motor-blower on determining that the patient interface is secured to the anchor.

Another aspect of one form of the present technology is the apparatus is configured to supply power to the controllable motor-blower on determining that the patient interface is not secured to the anchor.

Another aspect of one form of the present technology is a system comprising an apparatus for providing positive pressure respiratory therapy to a patient breathing in a respiratory cycle including an inhalation portion and an exhalation portion, comprising a controllable motor-blower configured to generate a supply of air at a positive pressure relative to ambient pressure by rotating an impeller at an impeller speed, a housing holding said motor-blower, wherein the housing comprises an anchor configured to secure the patient interface to the apparatus and a patient interface having a complementary structure that engages the anchor of the apparatus.

Another aspect of one form of the present technology is the complementary structure forms part of a mechanical connection with the anchor.

Another aspect of one form of the present technology is the complementary structure is magnetic.

Another aspect of one form of the present technology is the patient interface is structured to be oriented in an upright position when the anchor and the complementary structure are engaged.

An aspect of certain forms of the present technology is a medical device that is easy to use, e.g., by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment.

An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000 and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000 and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000 and passes along an air circuit 4170 to the patient 1000. The patient is sleeping in a side sleeping position.

4.2 Patient Interface

FIG. 2 shows a patient interface in the form of a nasal mask in accordance with one form of the present technology.

4.3 RPT Device

FIG. 3A shows an RPT device in accordance with one form of the present technology.

FIG. 3B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

5 DETAILED DESCRIPTION OF EXAMPLES OF THE TECHNOLOGY

Figure 1A:
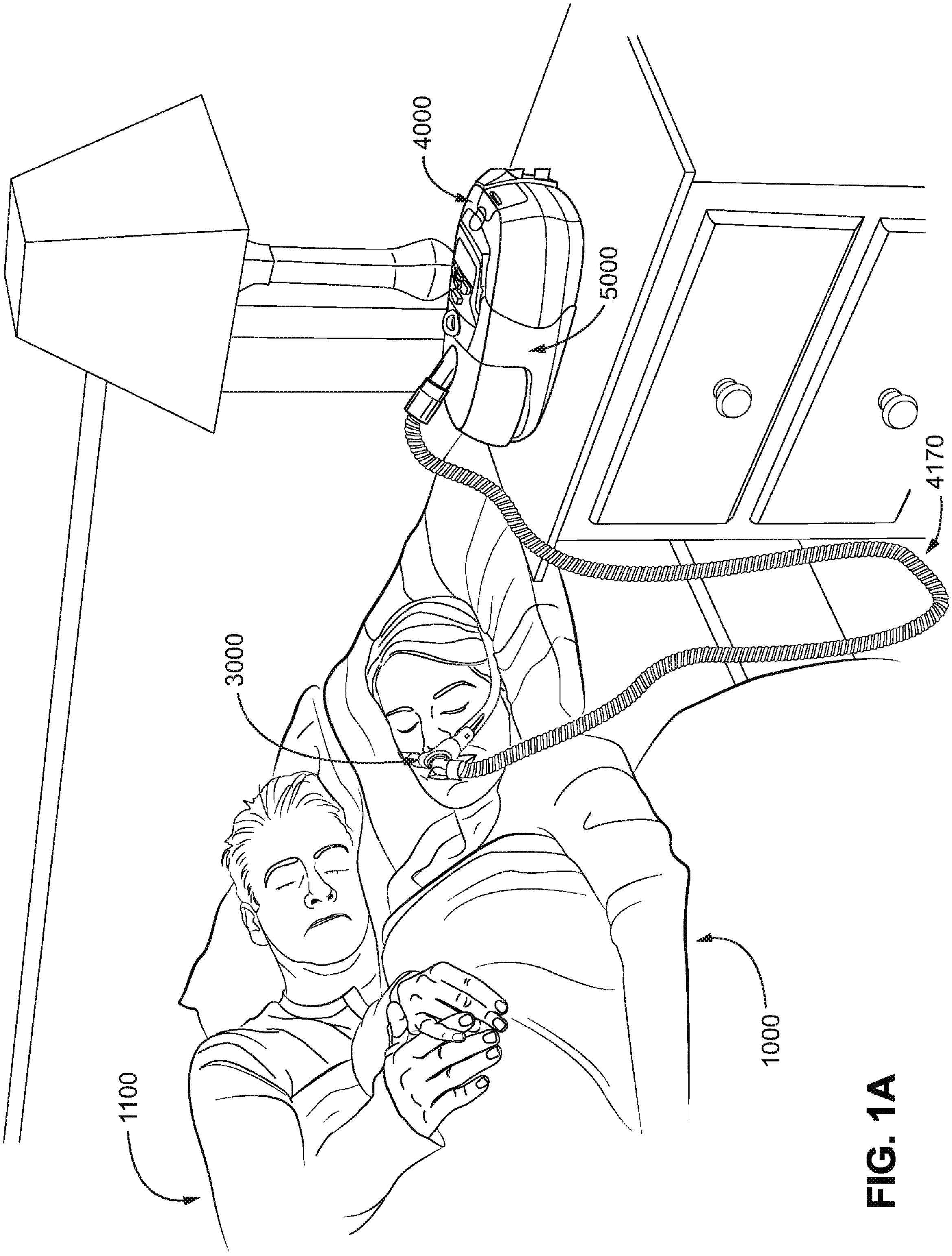
Figure 1B:
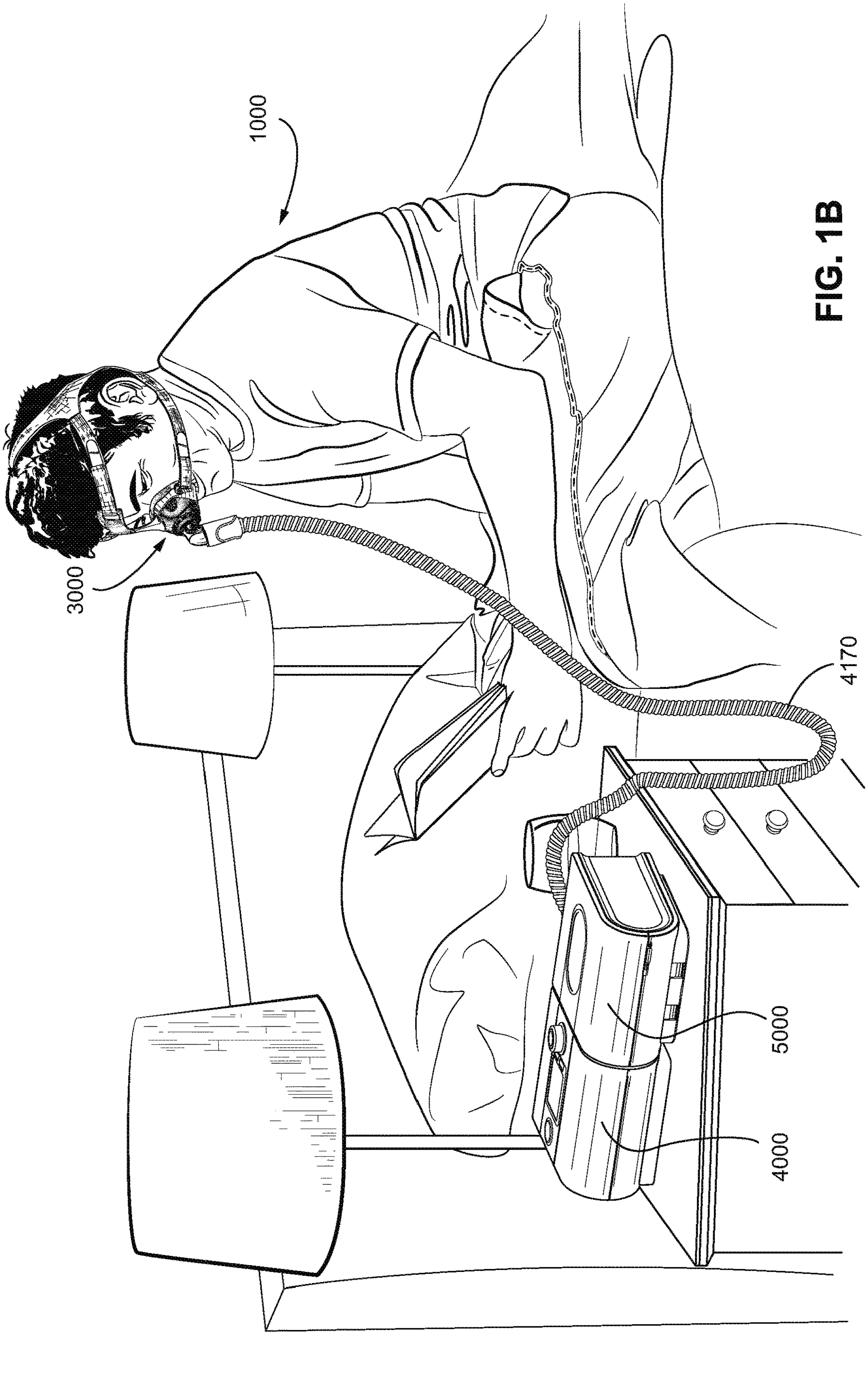
Figure 1C:
Figure 2:
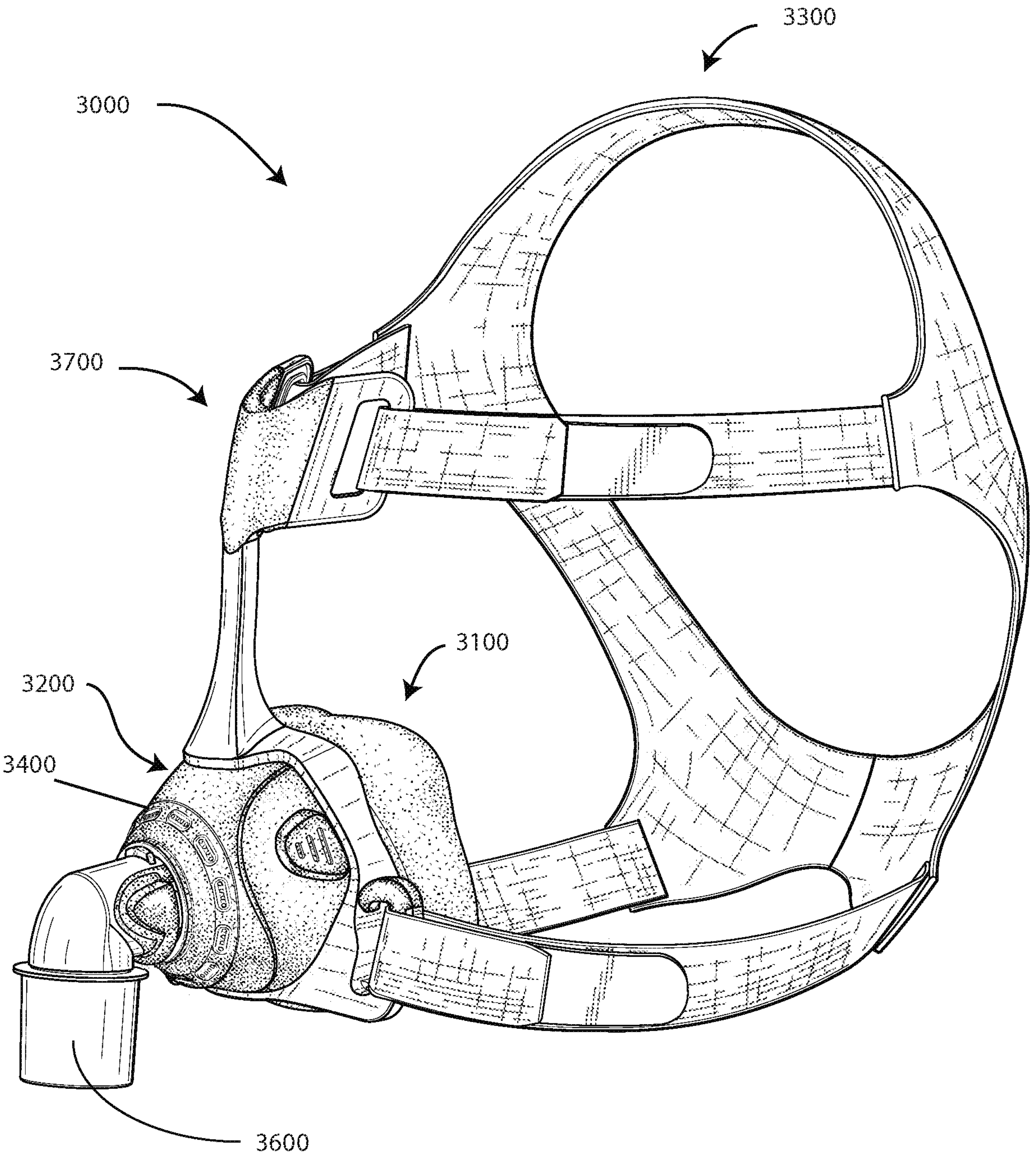

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700.

In some forms a functional aspect may be provided by one or more physical components.

In some forms, one physical component may provide one or more functional aspects.

In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

An example of an unsealed patient interface, in the form of a nasal cannula, includes nasal prongs which can deliver air to respective nares of the patient 1000 via respective orifices in their tips.

Such nasal prongs do not generally form a seal with the inner or outer skin surface of the nares. This type of interface results in one or more gaps that are present in use by design (intentional), but they are typically not fixed in size such that they may vary unpredictably by movement during use. This can present a complex pneumatic variable for a respiratory therapy system when pneumatic control and/or assessment is implemented, unlike other types of mask-based respiratory therapy systems.

The air to the nasal prongs may be delivered by one or more air supply lumens that are coupled with the nasal cannula-type unsealed patient interface. The lumens lead from the nasal cannula-type unsealed patient interface to a respiratory therapy device via an air circuit.

The unsealed patient interface is particularly suitable for delivery of flow therapies, in which the RPT device generates the flow of air at controlled flow rates rather than controlled pressures. The "vent" or gap at the unsealed patient interface, through which excess airflow escapes to ambient, is the passage between the end of the prongs of the nasal cannula-type unsealed patient interface via the patient's nares to atmosphere.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH2O with respect to ambient.

The patient interface 3000 in accordance with one form of the present technology is constructed and arranged to be able to provide a supply of air at a positive pressure of at least 10 cmH2O with respect to ambient.

The patient interface 3000 in accordance with one form of the present technology is constructed and arranged to be able to provide a supply of air at a positive pressure of at least 20 cmH2O with respect to ambient.

5.3.1 Seal-Forming Structure

In one form of the present technology, a seal-forming structure 3100 provides a target seal-forming region.

In one form of the present technology, the seal-forming structure may additionally provide a cushioning function.

The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face.

The pressure assisted mechanism may act in conjunction with elastic tension in the positioning and stabilising structure.

In one form, the seal-forming structure 3100 comprises a sealing flange and a support flange.

In one form, the sealing flange may comprise a relatively thin member with a thickness of less than about 1 mm, for example about 0.25 mm to about 0.45 mm, which extends around the perimeter of the plenum chamber 3200.

The support flange may be relatively thicker than the sealing flange. The support flange may be disposed between the sealing flange and the marginal edge of the plenum chamber 3200, and extend at least part of the way around the perimeter.

In some forms of the present technology, the support flange is or includes a spring-like element and functions to support the sealing flange from buckling in use.

In one form, the seal-forming structure may comprise a compression sealing portion.

In one form, the seal-forming structure may comprise a gasket sealing portion.

In use the compression sealing portion, or the gasket sealing portion is constructed and arranged to be in compression, e.g., as a result of elastic tension in the positioning and stabilising structure.

In one form, the seal-forming structure may comprise a tension portion. In use, the tension portion is held in tension, e.g., by adjacent regions of the sealing flange.

In one form, the seal-forming structure may comprise a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nasal Pillows

In one form, the seal-forming structure of the non-invasive patient interface 3000 may comprise a pair of nasal puffs, or nasal pillows, each nasal puff or nasal pillow being constructed and arranged to form a seal with a respective naris of the nose of a patient.

5.3.2 Plenum Chamber

The plenum chamber 3200 may have a perimeter that is shaped to be complementary to the surface contour of the face of an average person in the region where a seal will form in use.

In use, a marginal edge of the plenum chamber 3200 may be positioned in close proximity to an adjacent surface of the face.

Actual contact with the face may be provided by the seal-forming structure 3100.

The seal-forming structure 3100 may extend in use about the entire perimeter of the plenum chamber 3200.

In some forms, the plenum chamber 3200 and the seal-forming structure 3100 may be formed from a single homogeneous piece of material.

5.3.3 Positioning and Stabilising Structure

The seal-forming structure 3100 of the patient interface 3000 of the present technology may be held in sealing position in use by the positioning and stabilising structure 3300.

In one form, the positioning and stabilising structure 3300 may provide a retention force at least sufficient to overcome the effect of the positive pressure in the plenum chamber 3200 to lift off the face.

In one form, the positioning and stabilising structure 3300 may provide a retention force to overcome the effect of the gravitational force on the patient interface 3000.

In one form, the positioning and stabilising structure 3300 may provide a retention force as a safety margin to overcome the potential effect of disrupting forces on the patient interface 3000, such as from tube drag, or accidental interference with the patient interface.

In one form of the present technology, a positioning and stabilising structure 3300 may be configured in a manner consistent with being worn by a patient while sleeping.

In one example, the positioning and stabilising structure 3300 may have a low profile to reduce the perceived or actual bulk of the apparatus.

In one example, the positioning and stabilising structure 3300 may have a cross-sectional thickness that may reduce the perceived or actual bulk of the apparatus.

In one example, the positioning and stabilising structure 3300 may comprise at least one strap having a rectangular cross-section.

In one example, the positioning and stabilising structure 3300 may comprise at least one flat strap.

In one form of the present technology, a positioning and stabilising structure 3300 may be configured so as not to be too large and bulky to prevent the patient from lying in a supine sleeping position with a back region of the patient's head on a pillow.

In one form of the present technology, a positioning and stabilising structure 3300 may be configured so as not to be too large and bulky to prevent the patient from lying in a side sleeping position with a side region of the patient's head on a pillow.

In one form of the present technology, a positioning and stabilising structure 3300 may be provided with a decoupling portion located between an anterior portion of the positioning and stabilising structure 3300 and a posterior portion of the positioning and stabilising structure 3300.

In one form, the decoupling portion does not resist compression.

In one form, the decoupling portion may be a flexible or floppy strap.

In one form, the decoupling portion is constructed and arranged so that when the patient lies with their head on a pillow, the presence of the decoupling portion may prevent a force on the posterior portion from being transmitted along the positioning and stabilising structure 3300 and disrupting the seal.

In one form of the present technology, a positioning and stabilising structure 3300 may comprise a strap constructed from a laminate of a fabric patient-contacting layer, a foam inner layer and a fabric outer layer.

In one form, the foam may be porous to allow moisture, (e.g., sweat), to pass through the strap.

In one form, the fabric outer layer may comprise loop material to engage with a hook material portion.

In certain forms of the present technology, a positioning and stabilising structure 3300 may comprise a strap that is extensible.

In one form, the positioning and stabilising structure 3300 may comprise a strap that is resiliently extensible.

In one example, the strap may be configured in use to be in tension, and to direct a force to draw a seal-forming structure into sealing contact with a portion of a patient's face.

In one example, the strap may be configured as a tie.

In one form of the present technology, the positioning and stabilising structure 3300 may comprise a first tie.

In one form, the first tie may be constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure 3300 may include a second tie.

In one form, the second tie may be constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure 3300 may include a third tie that is constructed and arranged to interconnect the first tie and the second tie to reduce a tendency of the first tie and the second tie to move apart from one another.

In certain forms of the present technology, a positioning and stabilising structure 3300 may comprise a strap that is bendable.

In one form, the strap may be non-rigid.

An advantage of this aspect is that the strap may be more comfortable for a patient to lie upon while the patient is sleeping.

In certain forms of the present technology, a positioning and stabilising structure 3300 may comprise a strap constructed to be breathable to allow moisture vapour to be transmitted through the strap, In certain forms of the present technology, a system may comprise more than one positioning and stabilizing structure 3300.

In one form, each position and stabilizing structure 3300 may be configured to provide a retaining force to correspond to a different size and/or shape range.

In one example, the system may comprise one form of positioning and stabilizing structure 3300 suitable for a large sized head.

In one example, the system may comprise one form of positioning and stabilizing structure 3300 suitable for a small sized head.

5.3.4 Vent

In one form, the patient interface 3000 may include a vent 3400 constructed and arranged to allow for the washout of exhaled gases, e.g., carbon dioxide.

In one form, the vent 3400 may be located in the plenum chamber 3200.

In one form, the vent 3400 may be located in a decoupling structure.

In one form, the decoupling structure may be a swivel.

5.3.5 Decoupling Structure(s)

In one form the patient interface 3000 may include at least one decoupling structure.

In one form, the decoupling structure may be a swivel.

In one form, the decoupling structure may be a ball and socket.

5.3.6 Connection Port

Connection port 3600 may allow for connection to the air circuit 4170.

5.3.7 Forehead Support

In one form, the patient interface 3000 may include a forehead support 3700.

5.3.8 Anti-Asphyxia Valve

In one form, the patient interface 3000 may include an anti-asphyxia valve.

5.3.9 Ports

In one form of the present technology, a patient interface 3000 may include one or more ports that allow access to the volume within the plenum chamber 3200.

In one form, supplementary oxygen may be supplied to the plenum chamber 3200.

In one form, direct measurement of a property of gases within the plenum chamber 3200 may be made.

In one form, direct measurement of the pressure of gases within the plenum chamber 3200 may be made.

5.4 RPT Device

An RPT device 4000 in accordance with one aspect of the present technology may comprise mechanical, pneumatic, and/or electrical components.

In one form, the RPT device 4000 is configured to execute one or more algorithms 4300, such as any of the methods, in whole or in part, described herein.

In one form, the RPT device 4000 may be configured to generate a flow of air for delivery to a patient's airways, such as to treat one or more of the respiratory conditions described elsewhere in the present document.

In one form, the RPT device 4000 may be constructed and arranged to be capable of delivering a flow of air in a range of −20 L/min to +150 L/min while maintaining a positive pressure of at least 6 cmH2O, or at least 10 cmH2O, or at least 20 cmH2O.

In one form, the RPT device 4000 may have an external housing 4010, formed in two parts, an upper portion 4012 and a lower portion 4014.

In one form, the external housing 4010 may include one or more panel(s) 4015.

In one form, the RPT device 4000 may comprise a chassis 4016 that supports one or more internal components of the RPT device 4000.

In one form, the RPT device 4000 may include a handle 4018.

In one form of the present technology, the pneumatic path 4100 of the RPT device 4000 may comprise one or more air path items.

In one form, the air path items may include one or more of an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

In one form, one or more of the air path items may be located within a removable unitary structure which will be referred to as a pneumatic block 4020.

In one form, the pneumatic block 4020 may be located within the external housing 4010.

In one form, a pneumatic block 4020 may be supported by the chassis 4016.

In one form, a pneumatic block 4020 may be formed as part of the chassis 4016.

In one form the present technology, the RPT device 4000 may have an electrical power supply 4210.

In one form, the RPT device 4000 may have one or more electrical components 4200.

In one form, the electrical components 4200 may include one or more input devices 4220, a central controller 4230, a therapy device controller 4240, a pressure generator 4140, one or more protection circuits 4250, memory 4260, transducers 4270, data communication interface 4280 and/or one or more output devices 4290.

In one form, the electrical components 4200 may be mounted on a single Printed Circuit Board Assembly (PCBA) 4202.

In one form, the RPT device 4000 may include more than one PCBA 4202.

5.4.1 Anchor

The RPT device 4000 may comprise an anchor or retaining means arranged to releasably attach the patient interface 3000 to the RPT device.

The anchor may provide a site for securing the patient interface 3000 to the 4000 RPT device so that the patient interface 3000 can be reliably located when not in use. This may prevent the patient interface 3000 from being accidentally crushed by the user's body weight. This may also reduce the chances of the user dropping the patient interface 3000 and damaging it. The chance of dirt entering the air passages and/or contaminating the cushion may also be reduced.

In one form, the user can release the patient interface 3000 by gently tugging on the patient interface 3000 to release it from the RPT device 4000.

Figure 4:
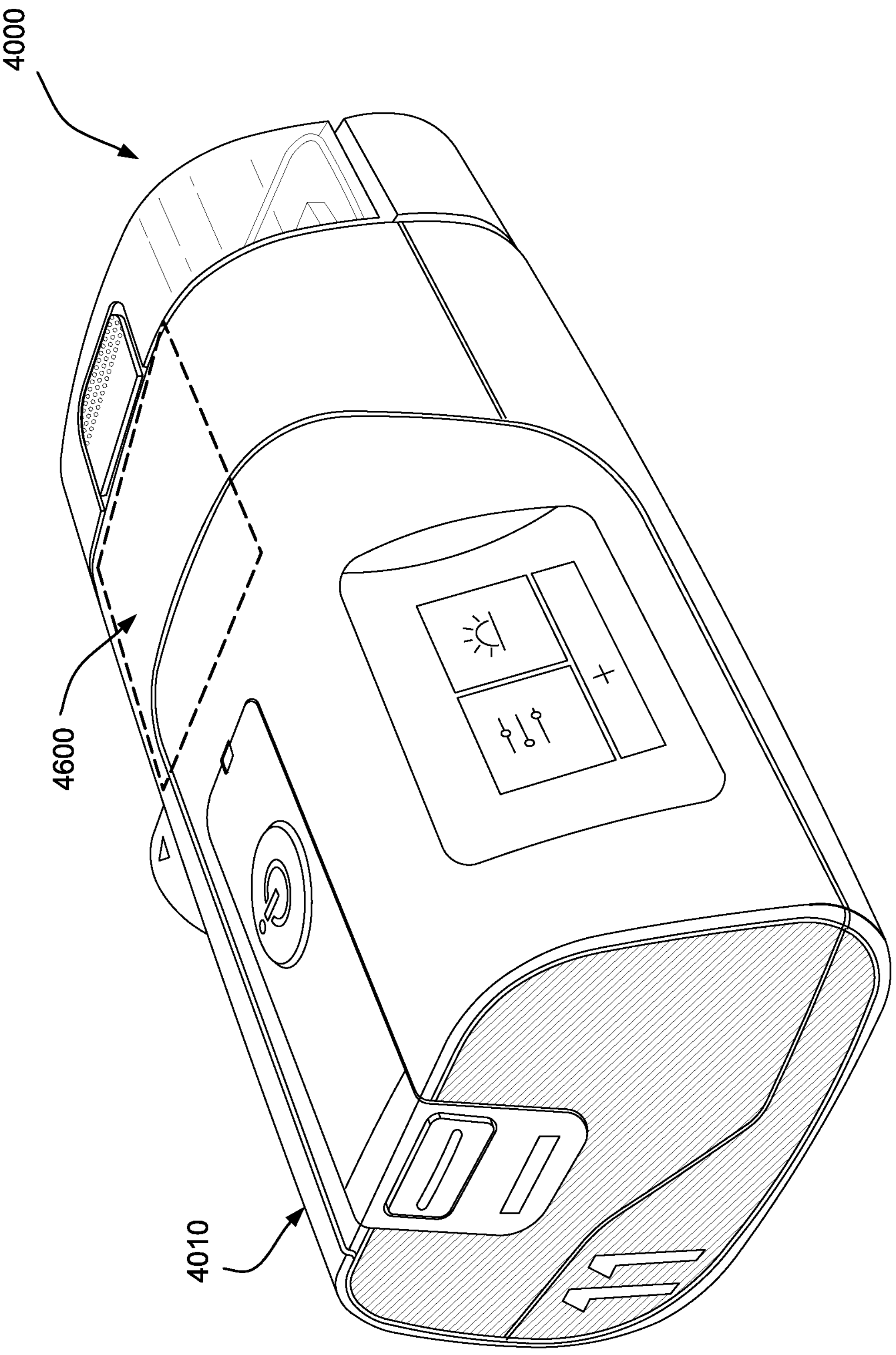
FIG. 4 shows an RPT device accordance with one form of the present technology.

As shown in FIG. 4, the anchor can be on the external housing 4010 of the RPT device 4000.

In one form, the anchor may be positioned on any surface of the external housing 4010 where it does not hinder a user from operating the RPT device 4010.

In one example, the anchor may be positioned where it does not hinder a user from removing the humidifier 5000 (which may comprise a water reservoir (also known as a humidifier tub) configured to hold, or retain, a volume of liquid (e.g., water) to be evaporated for humidification of the flow of air).

In one example, the anchor may be positioned where it does not obstruct a display screen of the display 4294.

In one example, the anchor can be on a top surface 4600 of the external housing 4010.

In one form of the present technology, the anchor may be a mechanical anchor.

In one example, the anchor may be a protrusion for engaging with tie or straps of the positioning and stabilising structure 3300.

In one example, the anchor may be a tie, a clip, a press stud, a strap, a hook and/or loop fastener.

In one example, the anchor may be an adhesive.

In one example, the anchor may include interlocking mechanism, such as a zip lock.

In one example, the anchor may be a fastener. Some suitable fasteners include a re-closable fastener, a hook and/or loop fastener, an electrostatic fastener, or any combination of thereof.

In one form of the present technology, the anchor may be a magnetic anchor. The magnetic anchor can be any form of magnet, such as permanent magnets, electromagnet magnets, and/or a combination of a magnet and a magnetic material.

In one example, the magnetic anchor can be positioned on the external housing 4010 of the RPT device 4000. Any surface of the external housing 4010 may provide a suitable location for the magnetic anchor.

In one example, the magnetic anchor can be positioned within the housing 4010 to magnetically engage the positioning and stabilising structure 3300 through the housing 4010.

In one form of the present technology, the anchor may be integral on the RPT device 4000 or housing 4010.

In one form of the present technology, the anchor may be provided as a removable attachment to the RPT device 4000 or housing 4010.

In some form, the patient interface 3000 may have a complementary structure or mating means for connecting with the anchor.

In one form, the complementary mating means form a mechanical connection with the anchor. For example, the complementary mating means may be a tie, a clip, a press stud, a strap, a hook and/or loop fastener. The complementary mating means on the patient interface may be on the first tie, second tie or third tie.

In one example, the patient interface 3000 may have a complementary magnet for attracting to a magnetic anchor. The magnets can be permanent magnets, electromagnet magnets, or a combination of a magnet and a magnetic material.

In one form of the present technology, the complementary mating means is configured to maximise the contact area of the anchor and the complementary mating means.

In one example, the complementary mating means may be a flat surface of the patient interface 3000.

In one example, the complementary mating means may be positioned on a flat surface of the patient interface 3000.

Figure 5:
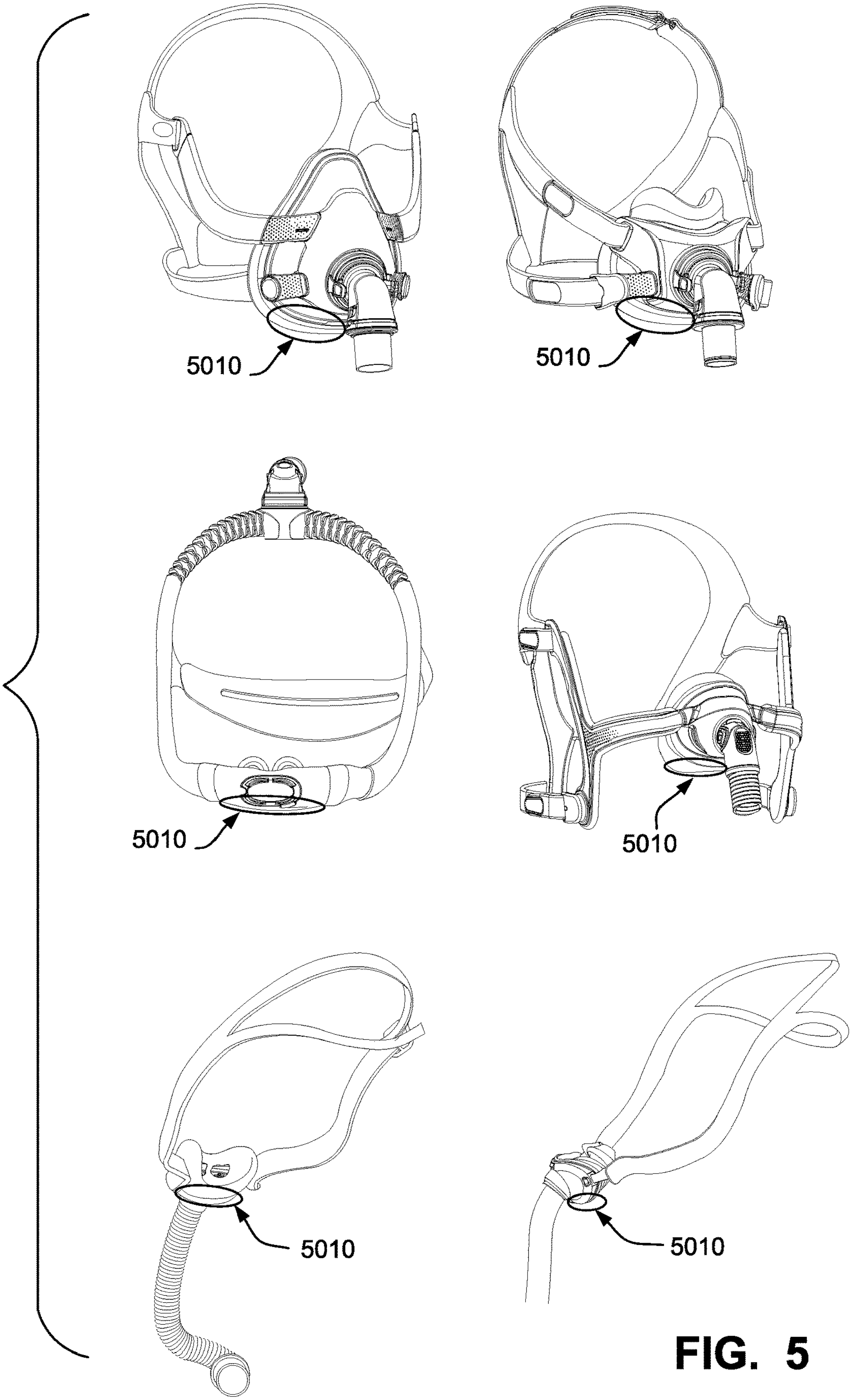
FIG. 5 shows patient interfaces with complementary mating means.

In one form, the complementary mating means may be on a bottom surface of the plenum chamber 3200 (when in use). FIG. 5 shows some examples of patient interfaces 3000 where the complementary mating means may be positioned (at 5010).

In one form of the present technology, the complementary mating means may be defined by the patient interface 3000. In one example, an existing feature of the patient interface 3000, such as the positioning and stabilising structure 3300 or plenum chamber 3200, may be used as the complementary mating means.

In one form, the complementary mating means may be integral on the patient interface 3000. In one example, the complementary mating means may be formed on the patient interface 3000.

In one form, the complementary mating means may be additionally provided as a removable attachment or accessory to the patient interface 3000.

In one form of the present technology, the patient interface 3000 may be oriented in an upright position when the anchor and complementary mating means are attached to each other. This may allow the patient interface to be conveniently positioned, low touch, and intuitive for use, even for new users.

In one form of the present technology, the anchor may be arranged on the RPT device 4000 to provide a clearance between the patient interface 3000 and the RPT device 4000 when the patient interface 3000 is attached. In one example, the anchor may be arranged such that there is a sufficient clearance between the plenum chamber 3200 and the RPT device to prevent contamination of the plenum chamber 3200.

In one form of the present technology, the anchor may be arranged on the RPT device 4000 to provide sufficient air flow to the patient interface 3000. This may allow for the trapped moisture and sweat on/in the patient interface 3000 to be sufficiently removed/dried.

In one form of the present technology, there may be physical contact between the anchor and the complementary mating means or between the anchor and the patient interface 3000. In this regard, the anchor and the mating means may physically touch each other in order to secure the patient interface to the RPT device.

In one form, the complementary mating means may be configured to attract a magnetic anchor. In one example, the mating means may have a magnet with an unlike pole and/or may have a magnetic material in order for attraction to the magnetic anchor. In some form, the contact is mechanical.

In one form of the present technology, the anchor and the complementary mating means may be in contact in a contactless manner. For example, there may be no physical contact between the anchor and the mating means.

In one form, the complementary mating means may be configured to repel a magnetic anchor.

In one example, the mating means may have a magnet with the same pole such that repelling force holds the patient interface 3000 in close proximity to the RPT device 4000.

In one example, the complementary mating means can be floated on top of the anchor.

5.4.2 Smart Connector

In one form of the technology, the anchor may be a connector for electrical communication between the sensors and/or actuators in the patient interface 3000 and an external computing device. The connector may relay data from the sensors and/or actuators in the patient interface 3000 to an external computing device.

In one form, the external computing device may be the central controller 4230 of the RPT device 4000.

In one form, the RPT device 4000 may comprise a data access port to transfer data from the patient interface 3000 to another computing device such as a smartphone of the patient and/or a monitoring server that is operated by or accessible to a clinician or other healthcare provider.

In one example, the data relayed may comprise information collected when the patient interface 3000 is in use, such as overnight when the user is sleeping. Examples of data may include true mask usage duration, true leak data, true therapy pressure in mask, O2/CO2 level trends in the mask, sleep positions, or a combination thereof.

In some form, the data relates to breathomics for health monitoring and/or disease detection.

In one example, data such as breathed-out biomarker and/or its amounts can be relayed to an external computing device when connected to the anchor.

In one form of the present technology, a patient interface 3000 may be configured to measure the patient's physiological and sleep data.

In one form, the patient interface 3000 may have one or more sensors and/or actuators provided therein.

In one example, one or more sensors and one or more actuators may respectively be embedded within the patient interface, such as between textile layers of headgear of the patient interface.

In one example, one or more sensors and one or more actuators may respectively be attached to internal and/or external surfaces of the headgear or other components of the patient interface. In one form, one or more sensors and/or actuators may be integrated in a positioning and stabilising structure 3300, and/or in another component such as a seal-forming structure or plenum chamber 3200.

In some forms, the headgear may comprise one or more leads, cables, or other electrically conductive elements extending therefrom and being in electrical communication with one or more of the sensors or actuators. Each such electrically conductive element may comprise a terminal that can contact skin of the wearer of the headgear to provide one or more suitable signal grounding points on the face or head of the wearer, such as behind the ear, or below the eye socket. This may be useful for implementation of an EEG, EMG, or EOG system within the headgear.

Sensors embedded in the patient interface 3000 may help collect sleep-related data and physiological indicators, such as vital data. In some forms, this can be used to determine the improvement in sleep and health by comparing data before and after start of therapy. This data can be processed, and the patient informed of how the therapy is improving sleep.

In one example, a patient may wear a patient interface 3000 with integrated sensors, before commencing therapy, during sleep (physiological and sleep data may be recorded), and/or when awake (in the case of physiological data). The data recorded during these events can be analysed to provide a comprehensive treatment to the user. The physiological and sleep data may be communicated to external computing devices such as a smartphone of the patient, RPT device, and/or a monitoring server that is operated by or accessible to a clinician or other healthcare provider.

With a smoother acclimatisation and streamlined transfer of data without substantial input from the user, patient compliance is more likely.

The data collected may also be useful in determining population-level sleep and/or physiological characteristics of one or more cohorts of patients undergoing respiratory therapy, thereby potentially enabling better customisation of therapy to patients falling within particular categories, or otherwise enabling optimisation of operation of an RPT device 4000.

Additionally, such data can be fed back into the central controller 4230 such that the one or more algorithms 4300 can be fine-tuned to be suitable for each patient depending on individual habits.

Figure 3A:
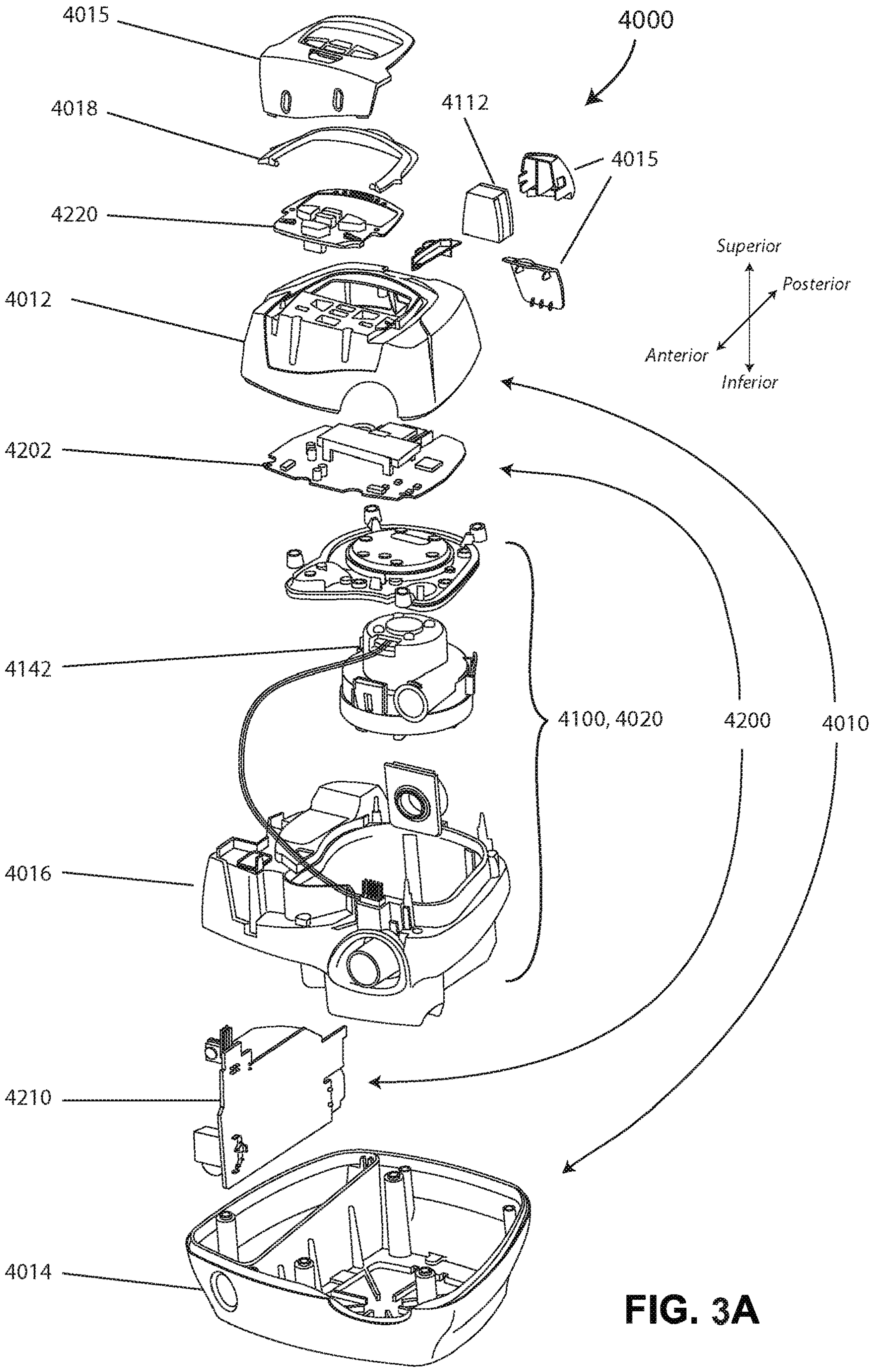
FIG. 3C is a schematic diagram of the electrical components of an RPT device in accordance with one form of the present technology.
FIG. 3D is a schematic diagram of the algorithms implemented in an RPT device in accordance with one form of the present technology.
FIG. 3E is a flow chart illustrating a method carried out by the therapy engine module of FIG. 3D in accordance with one form of the present technology.
Figure 3B:
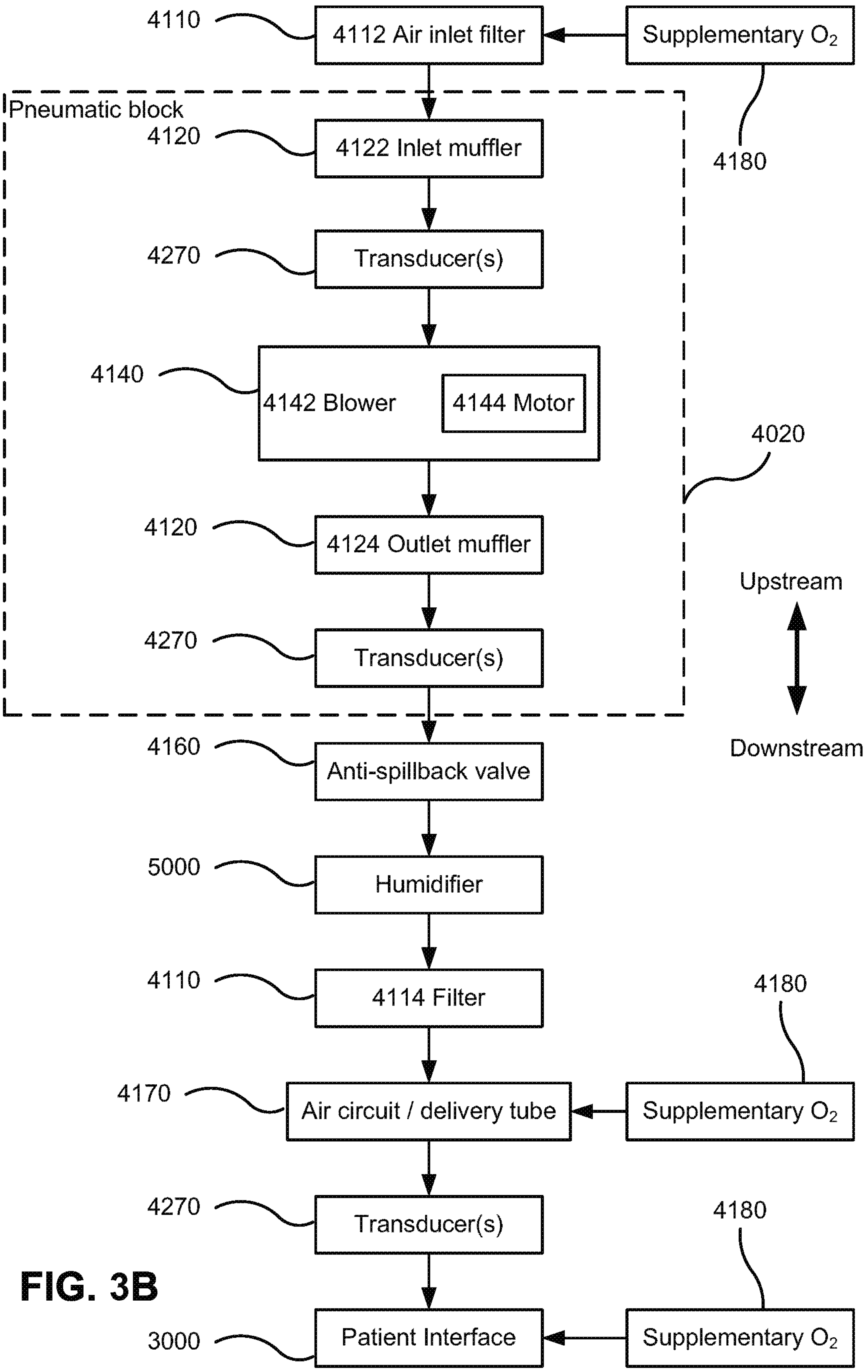
Figure 3C:
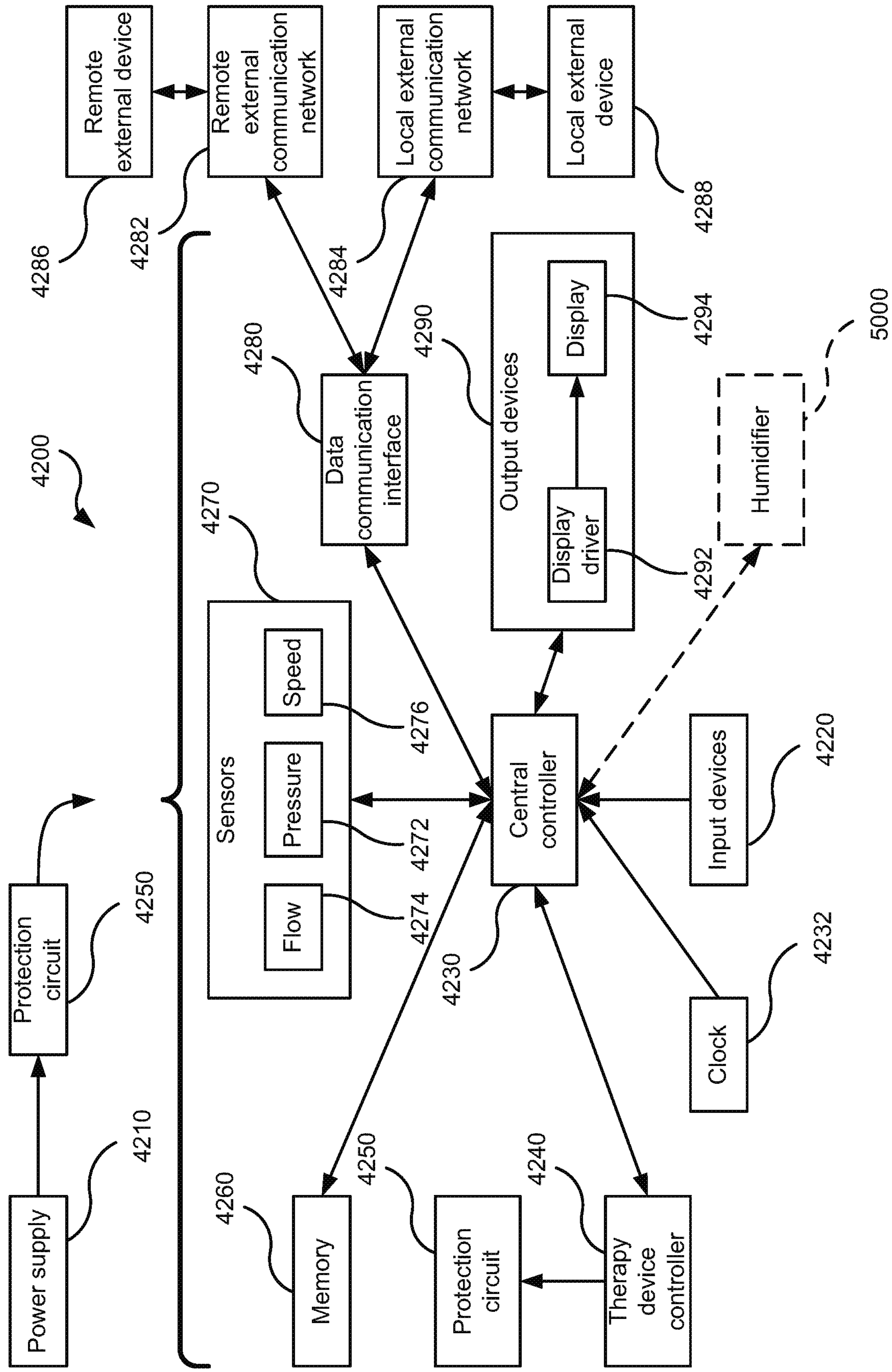
Figure 3D:
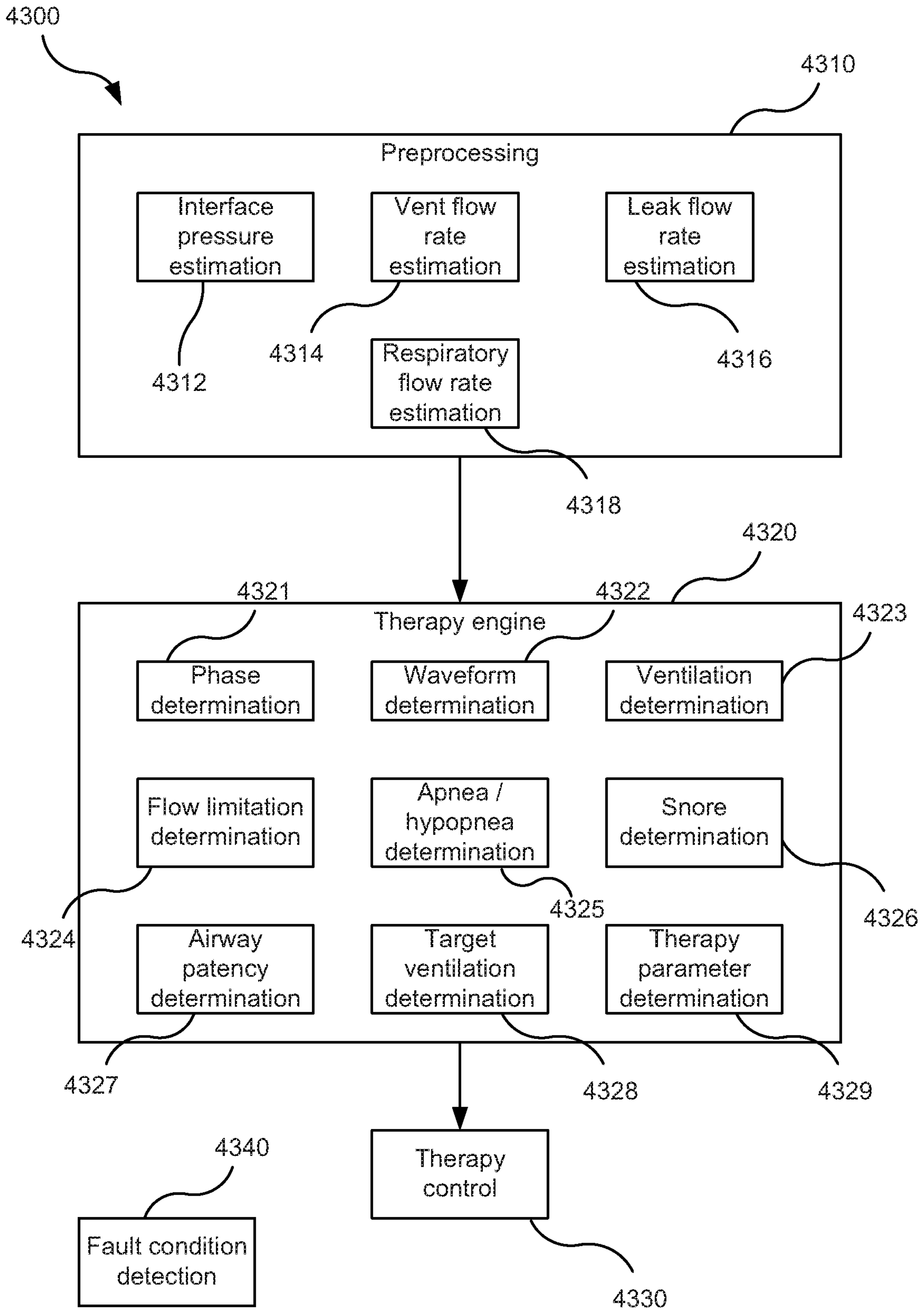

In some forms of the present technology, measurement of functional parameters at the patient side using sensors integrated in and/or attached to the mask may provide improved. In one form, active feedback-based control of an RPT device 4000 to which the patient interface 3000 is connected may improve feedback control of a pressure generator 4140 of the RPT device 4000 (FIG. 3B).

In some forms of the present technology, the sleep stage information may be transmitted to RPT device 4000, such that it can be used by pressure generator 4140 to adjust the therapy pressures to avoid arousal or obstruction events.

In some forms of the present technology, the anchor may include a charger, such as a charging means, for charging a battery module in the patient interface 3000. The battery module can be used to power the sensors and/or actuators in the patient interface 3000. The charging can be via wireless charging, which can be inductive charging, resonant inductive charging and/or radio frequency-based charging.

In some forms, the patient interface 3000 can be wirelessly connected to the RPT device 4000 via the anchor.

In one example, in inductive charging, an alternating magnetic field generated in a transmitting coil is used to electromagnetically induce electricity in a receiving coil.

In one example, resonant charging, or magnetic resonance charging, is an extended form of inductive charging and relies on resonant coils to provide magnetic resonance between a transmitting coil and a receiving coil. Resonant charging has advantages in that power is transmissible at a relatively great distance, there is a certain degree of freedom with respect to an alignment between the coils, and multiple devices can charge simultaneously. These benefits serve to improve convenience of us and create a better experience for end users.

5.4.3 RPT Device Mechanical & Pneumatic Components

An RPT device 4000 may comprise one or more of the following components in an integral unit. In an alternative form, one or more of the following components may be located as respective separate units.

5.4.3.1 Air Filter(s)

In one form of the present technology, an RPT device 4000 may include an air filter 4110.

In one form, an RPT device 4000 may include a plurality of air filters 4110.

In one form, an inlet air filter 4112 may be located at the beginning of the pneumatic path upstream of a pressure generator 4140.

In one form, an outlet air filter 4114, such as an antibacterial filter, may be located between an outlet of the pneumatic block 4020 and a patient interface 3000.

5.4.3.2 Muffler(s)

In one form of the present technology, an RPT device 4000 may include a muffler 4120.

In one form, an RPT device 4000 may include plurality of mufflers 4120.

In one form of the present technology, an inlet muffler 4122 may be located in the pneumatic path upstream of a pressure generator 4140.

In one form of the present technology, an outlet muffler 4124 may be located in the pneumatic path between the pressure generator 4140 and a patient interface 3000.

5.4.3.3 Pressure Generator

In one form of the present technology, a pressure generator 4140 for producing a flow, or a supply, of air at positive pressure is a controllable blower 4142. For example, the blower 4142 may include a brushless DC motor 4144 with one or more impellers. The impellers may be located in a volute.

In one form, the blower may be capable of delivering a supply of air, for example at a rate of up to about 120 litres/minute, at a positive pressure in a range from about 4 cmH2O to about 20 cmH2O, or in other forms up to about 30 cmH2O when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 may be under the control of the therapy device controller 4240.

In one form, a pressure generator 4140 may be a piston-driven pump.

In one form, a pressure generator 4140 may be a pressure regulator connected to a high-pressure source, such as a compressed air reservoir.

In one form, a pressure generator 4140 may be a bellows.

5.4.3.4 Transducer(s)

In one form of the present technology, the RPT device may include one or more transducers. In one example, one or more transducers may be internal of the RPT device.

In one example, one or more transducers may be external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.3.4.1 Flow Rate Sensor

A flow rate sensor 4274 in accordance with the present technology may be based on a differential pressure transducer, for example, an SDP600 Series differential pressure transducer from SENSIRION.

In one form, a signal generated by the flow rate sensor 4274 and representing a flow rate may be received by the central controller 4230.

5.4.3.4.2 Pressure Sensor

A pressure sensor 4272 in accordance with the present technology may be located in fluid communication with the pneumatic path.

In one example, the pressure sensor may be a transducer from the HONEYWELL ASDX series.

In one example, the pressure sensor may be a transducer from the NPA Series from GENERAL ELECTRIC.

In one form, a signal generated by the pressure sensor 4272 and representing a pressure may be received by the central controller 4230.

5.4.3.4.3 Motor Speed Transducer

In one form of the present technology a motor speed transducer 4276 may be used to determine a rotational velocity of the motor 4144 and/or the blower 4142. In one example, a motor speed signal from the motor speed transducer 4276 may be provided to the therapy device controller 4240. The motor speed transducer 4276 may, for example, be a speed sensor, such as a Hall effect sensor.

5.4.3.5 Anti-Spill Back Valve

In one form of the present technology, an anti-spill back valve 4160 may be located between the humidifier 5000 and the pneumatic block 4020. The anti-spill back valve may be constructed and arranged to reduce the risk that water will flow upstream from the humidifier 5000, for example to the motor 4144.

5.4.4 RPT Device Electrical Components

5.4.4.1 Power Supply

In one form of the present technology, the RPT device 4000 may comprise a power supply 4210.

In one example, a power supply 4210 may be located internal of the RPT device 4000.

In one example, a power supply 4210 may be external of the external housing 4010 of the RPT device 4000.

In one form of the present technology, power supply 4210 may provide electrical power to the RPT device 4000 only.

In one form of the present technology, power supply 4210 may provide electrical power to both RPT device 4000 and humidifier 5000.

5.4.4.2 Input Devices

In one form of the present technology, an RPT device 4000 may include one or more input devices 4220 in the form. For example, the one or more input devices may include one or more of buttons, switches or dials to allow a person to interact with the device.

In one form, an input device 4220 may be a physical device, such as physical button, switch or dial.

In one form, an input device 4220 may be a software device, such as a button, switch or dial accessible via a touch screen.

In one form, an input device 4220 may be physically connected to the external housing 4010.

In one form, an input device 4220 may be in wireless communication with a receiver that is in electrical connection to the central controller 4230.

In one form, an input device 4220 may be constructed and arranged to allow a person to select a value and/or a menu option.

5.4.4.3 Central Controller

In one form of the present technology, the central controller 4230 may comprise one or a plurality of processors suitable to control an RPT device 4000.

In one example, a processor may include an x86 INTEL processor, a processor based on ARM® Cortex®-M processor from ARM Holdings such as an STM32 series microcontroller from ST MICROELECTRONIC.

In one example, a processor may include a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS.

In one form of the present technology, the central controller 4230 may be a dedicated electronic circuit.

In one form, the central controller 4230 may be an application-specific integrated circuit.

In one form, the central controller 4230 may comprise discrete electronic components.

In one form of the present technology, the central controller 4230 may be configured to receive input signal(s) from one or more transducers 4270, one or more input devices 4220, and/or the humidifier 5000.

In one form of the present technology, the central controller 4230 may be configured to provide output signal(s) to one or more of an output device 4290, a therapy device controller 4240, a data communication interface 4280, and/or the humidifier 5000.

In some forms of the present technology, the central controller 4230 may be configured to implement one or more methodologies described herein, such as one or more algorithms 4300 which may be implemented with processor-control instructions, expressed as computer programs stored in a non-transitory computer readable storage medium, such as memory 4260.

In some forms of the present technology, the central controller 4230 may be integrated with an RPT device 4000.

In some forms of the present technology, some methodologies may be performed by a remotely located device. In one example, a remotely located device may determine control settings for a ventilator or detect respiratory related events by analysis of stored data such as from any of the sensors described herein.

In some forms of the present technology, the RPT device 4000 may determine whether or not a patient interface 3000 is secured to the anchor. For example, the controller 4230 may determine whether the patient interface 3000 is secured to the anchor 3000 and whether the patient interface 3000 is not secured to the anchor 3000.

In one form, this determination can be based on changes in magnetic field at or surrounding the anchor.

In one example, when the anchor is a magnetic anchor, coupling of the patient interface to the magnetic anchor can cause the magnetic field to be varied, thus indicating that the patient interface is "not-in-use."

In one example, the magnetic field being unvaried may indicate that the patient interface is "in use."

In one form, the determination can be based on the changes in electrical current at or surrounding the anchor. For example, changes in electrical current may provide an indication that the patient interface is connected and data from the patient interface can be relayed, or the battery in the patient interface can be charged.

In some forms, the controller 4230 may be configured to cut power to the controllable motor-blower when it is determined that the patient interface 3000 is secured to the anchor. In this configuration, the patient interface 3000 is in a "not-in-use" position.

In some forms of the present technology, the controller 4230 may be configured to supply power to the controllable motor-blower when it is determined that the patient interface 3000 is not secured to the anchor. In this configuration, the patient interface 3000 is in a "use" position.

5.4.4.4 Clock

The RPT device 4000 may include a clock 4232 that is connected to the central controller 4230.

5.4.4.5 Therapy Device Controller

In one form of the present technology, therapy device controller 4240 may be a therapy control module 4330 that forms part of the algorithms 4300 executed by the central controller 4230.

In one form of the present technology, therapy device controller 4240 may be a dedicated motor control integrated circuit. For example, in one form a MC33035 brushless DC motor controller, manufactured by ONSEMI is used.

5.4.4.6 Protection Circuits

The one or more protection circuits 4250 in accordance with the present technology may comprise an electrical protection circuit, a temperature and/or pressure safety circuit.

5.4.4.7 Memory

In accordance with one form of the present technology the RPT device 4000 may include memory 4260, e.g., nonvolatile memory. In some forms, memory 4260 may include battery powered static RAM. In some forms, memory 4260 may include volatile RAM.

In some forms, memory 4260 may be located on the PCBA 4202.

In some forms, memory 4260 may be in the form of EEPROM, or NAND flash.

In one form of the present technology, RPT device 4000 may include a removable form of memory 4260, such as a memory card made in accordance with the Secure Digital (SD) standard.

In one form of the present technology, the memory 4260 may act as a non-transitory computer readable storage medium on which is stored computer program instructions expressing the one or more methodologies described herein, such as the one or more algorithms 4300.

5.4.4.8 Data Communication Systems

In one form of the present technology, a data communication interface 4280 may be provided, and may be connected to the central controller 4230.

In one form, data communication interface 4280 may be connectable to a remote external communication network 4282 and/or a local external communication network 4284.

In one example, the remote external communication network 4282 may be connectable to a remote external device 4286.

In one example, the local external communication network 4284 may be connectable to a local external device 4288.

In one form, data communication interface 4280 may be part of the central controller 4230.

In one form, data communication interface 4280 may be separate from the central controller 4230 and may comprise an integrated circuit or a processor.

In one form, a remote external communication network 4282 may be the Internet. The data communication interface 4280 may use wired communication (e.g., via Ethernet, or optical fibre) or a wireless protocol (e.g. CDMA, GSM, LTE) to connect to the Internet.

In one form, a local external communication network 4284 may utilise one or more communication standards, such as Bluetooth, or a consumer infrared protocol.

In one form, remote external device 4286 is one or more computers, for example a cluster of networked computers. Such a remote external device 4286 may be accessible to an appropriately authorised person such as a clinician.

In one form, remote external device 4286 may be virtual computers, rather than physical computers. Such a remote external device 4286 may be accessible to an appropriately authorised person such as a clinician.

The local external device 4288 may be any suitable electronic device, such as a personal computer, mobile phone, tablet or remote control.

5.4.4.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.4.9.1 Display Driver

A display driver 4292 may receive as an input the characters, symbols, or images intended for display on the display 4294, and convert them to commands that cause the display 4294 to display those characters, symbols, or images.

5.4.4.9.2 Display

A display 4294 may be configured to visually display characters, symbols, or images in response to commands received from the display driver 4292. For example, the display 4294 may be an eight-segment display, in which case the display driver 4292 may convert each character or symbol, such as the figure "0", to eight logical signals indicating whether the eight respective segments are to be activated to display a particular character or symbol.

5.4.5 RPT Device Algorithms

In some forms of the present technology, the central controller 4230 may be configured to implement one or more algorithms 4300 expressed as computer programs stored in a non-transitory computer readable storage medium, such as memory 4260. The algorithms 4300 may be generally grouped into groups referred to as modules.

In some forms of the present technology, some portion or all of the algorithms 4300 may be implemented by a controller of an external device such as the local external device 4288 or the remote external device 4286. In such forms, data representing the input signals and/or intermediate algorithm outputs necessary for the portion of the algorithms 4300 to be executed at the external device may be communicated to the external device via the local external communication network 4284 or the remote external communication network 4282.

In such forms, the portion of the algorithms 4300 to be executed at the external device may be expressed as computer programs, such as with processor control instructions to be executed by one or more processor(s), stored in a non-transitory computer readable storage medium accessible to the controller of the external device. Such programs configure the controller of the external device to execute the portion of the algorithms 4300.

In such forms, the therapy parameters generated by the external device via the therapy engine module 4320 (if such forms part of the portion of the algorithms 4300 executed by the external device) may be communicated to the central controller 4230 to be passed to the therapy control module 4330.

5.4.5.1 Pre-Processing Module

A pre-processing module 4310 in accordance with one form of the present technology may receive as an input a signal from a transducer 4270, such as a flow rate sensor 4274 or pressure sensor 4272, and perform one or more process steps to calculate one or more output values that will be used as an input to another module, such as a therapy engine module 4320.

In one form of the present technology, the output values may include the interface pressure Pm, the vent flow rate Qv, the respiratory flow rate Qr, and/or the leak flow rate Ql.

In various forms of the present technology, the pre-processing module 4310 may comprise one or more of the following algorithms interface pressure estimation 4312, vent flow rate estimation 4314, leak flow rate estimation 4316, and/or respiratory flow rate estimation 4318.

5.4.5.1.1 Interface Pressure Estimation

In one form of the present technology, an interface pressure estimation algorithm 4312 may receive as inputs a signal from the pressure sensor 4272 indicative of the pressure in the pneumatic path proximal to an outlet of the pneumatic block (the device pressure Pd) and a signal from the flow rate sensor 4274 representative of the flow rate of the airflow leaving the RPT device 4000 (the device flow rate Qd). The device flow rate Qd, absent any supplementary gas 4180, may be used as the total flow rate Qt. The interface pressure algorithm 4312 may estimate the pressure drop $\Delta P$ through the air circuit 4170. The dependence of the pressure drop $\Delta P$ on the total flow rate Qt may be modelled for the particular air circuit 4170 by a pressure drop characteristic $\Delta P(Q)$. The interface pressure estimation algorithm, 4312 then may provide as an output an estimated pressure, Pm, in the patient interface 3000. The pressure, Pm, in the patient interface 3000 may be estimated as the device pressure Pd minus the air circuit pressure drop $\Delta P$.

5.4.5.1.2 Vent Flow Rate Estimation

In one form of the present technology, a vent flow rate estimation algorithm 4314 may receive as an input an estimated pressure, Pm, in the patient interface 3000 from the interface pressure estimation algorithm 4312 and estimate a vent flow rate of air, Qv, from a vent 3400 in a patient interface 3000. The dependence of the vent flow rate Qv on the interface pressure Pm for the particular vent 3400 in use may be modelled by a vent characteristic Qv(Pm).

5.4.5.1.3 Leak Flow Rate Estimation

In one form of the present technology, a leak flow rate estimation algorithm 4316 may receive as an input a total flow rate, Qt, and a vent flow rate Qv, and provide as an output an estimate of the leak flow rate Ql. In one form, the leak flow rate estimation algorithm may estimate the leak flow rate Ql by calculating an average of the difference between total flow rate Qt and vent flow rate Qv over a period sufficiently long to include several breathing cycles, e.g., about 10 seconds.

In one form, the leak flow rate estimation algorithm 4316 may receive as an input a total flow rate Qt, a vent flow rate Qv, and an estimated pressure, Pm, in the patient interface 3000, and provide as an output a leak flow rate Ql, by calculating a leak conductance, and determining a leak flow rate Ql to be a function of leak conductance and pressure, Pm. Leak conductance may be calculated as the quotient of low pass filtered non-vent flow rate equal to the difference between total flow rate Qt and vent flow rate Qv, and low pass filtered square root of pressure Pm, where the low pass filter time constant has a value sufficiently long to include several breathing cycles, e.g. about 10 seconds. The leak flow rate Ql may be estimated as the product of leak conductance and a function of pressure, Pm.

5.4.5.1.4 Respiratory Flow Rate Estimation

In one form of the present technology, a respiratory flow rate estimation algorithm 4318 may receive as an input a total flow rate, Qt, a vent flow rate, Qv, and a leak flow rate, Ql, and estimate a respiratory flow rate of air, Qr, to the patient, by subtracting the vent flow rate Qv and the leak flow rate Ql from the total flow rate Qt.

5.4.5.2 Therapy Engine Module

In one form of the present technology, a therapy engine module 4320 may receive as inputs one or more of a pressure, Pm, in a patient interface 3000, and a respiratory flow rate of air to a patient, Qr, and provide as an output one or more therapy parameters.

In one form of the present technology, a therapy parameter may be a treatment pressure Pt.

In one form of the present technology, therapy parameters may be one or more of an amplitude of a pressure variation, a base pressure, and/or a target ventilation.

In various forms, the therapy engine module 4320 may comprise one or more of the following algorithms phase determination 4321, waveform determination 4322, ventilation determination 4323, inspiratory flow limitation determination 4324, apnea/hypopnea determination 4325, snore determination 4326, airway patency determination 4327, target ventilation determination 4328, and/or therapy parameter determination 4329.

5.4.5.2.1 Phase Determination

In one form of the present technology, the RPT device 4000 may not determine phase.

In one form of the present technology, a phase determination algorithm 4321 may receive as an input a signal indicative of respiratory flow rate, Qr, and provide as an output a phase $\Phi$ of a current breathing cycle of a patient 1000.

In some forms, such as discrete phase determination, the phase output □ may be a discrete variable. One implementation of discrete phase determination may provide a bi-valued phase output $\Phi$ with values of either inhalation or exhalation, for example represented as values of 0 and 0.5 revolutions respectively, upon detecting the start of spontaneous inhalation and exhalation respectively. RPT devices 4000 that "trigger" and "cycle" may effectively perform discrete phase determination, since the trigger and cycle points are the instants at which the phase changes from exhalation to inhalation and from inhalation to exhalation, respectively.

In one form of bi-valued phase determination, the phase output $\Phi$ may be determined to have a discrete value of 0 (thereby "triggering" the RPT device 4000) when the respiratory flow rate Qr has a value that exceeds a positive threshold, and a discrete value of 0.5 revolutions (thereby "cycling" the RPT device 4000) when a respiratory flow rate Qr has a value that is more negative than a negative threshold. The inhalation time Ti and the exhalation time Te may be estimated as typical values over many respiratory cycles of the time spent with phase $\Phi$ equal to 0 (indicating inspiration) and 0.5 (indicating expiration) respectively.

In one form, a discrete phase determination may provide a tri-valued phase output $\Phi$ with a value of one of inhalation, mid-inspiratory pause, and exhalation.

In some forms, such as continuous phase determination, the phase output $\Phi$ may be a continuous variable, for example varying from 0 to 1 revolutions, or 0 to $2\pi$ radians. RPT devices 4000 that perform continuous phase determination may trigger and cycle when the continuous phase reaches 0 and 0.5 revolutions, respectively. In one form of continuous phase determination, a continuous value of phase $\Phi$ is determined using a fuzzy logic analysis of the respiratory flow rate Qr. A continuous value of phase determined in this implementation is often referred to as "fuzzy phase".

In one form of a fuzzy phase determination algorithm 4321, the following rules may be applied to the respiratory flow rate Qr:

1. If Qr is zero and increasing fast then $\Phi$ is 0 revolutions.
2. If Qr is large positive and steady then $\Phi$ is 0.25 revolutions.
3. If Qr is zero and falling fast, then $\Phi$ is 0.5 revolutions.
4. If Qr is large negative and steady then $\Phi$ is 0.75 revolutions.
5. If Qr is zero and steady and the 5-second low-pass filtered absolute value of Qr is large then $\Phi$ is 0.9 revolutions.
6. If Qr is positive and the phase is expiratory, then $\Phi$ is 0 revolutions.
7. If Qr is negative and the phase is inspiratory, then $\Phi$ is 0.5 revolutions.
8. If the 5-second low-pass filtered absolute value of Qr is large, $\Phi$ is increasing at a steady rate equal to the patient's breathing rate, low-pass filtered with a time constant of 20 seconds.

The output of each rule may be represented as a vector whose phase is the result of the rule and whose magnitude is the fuzzy extent to which the rule is true. The fuzzy extent to which the respiratory flow rate is "large", "steady", etc. is determined with suitable membership functions. The results of the rules, represented as vectors, may then be combined by some function such as taking the centroid. In such a combination, the rules may be equally weighted, or differently weighted.

In another implementation of continuous phase determination, the phase $\Phi$ may be first discretely estimated from the respiratory flow rate Qr as described above, as are the inhalation time Ti and the exhalation time Te. The continuous phase $\Phi$ at any instant may be determined as the half the proportion of the inhalation time Ti that has elapsed since the previous trigger instant, or 0.5 revolutions plus half the proportion of the exhalation time Te that has elapsed since the previous cycle instant (whichever instant was more recent).

5.4.5.2.2 Waveform Determination

In one form of the present technology, the therapy parameter determination algorithm 4329 may provide an approximately constant treatment pressure throughout a respiratory cycle of a patient.

In some forms of the present technology, the therapy control module 4330 may control the pressure generator 4140 to provide a treatment pressure Pt that varies as a function of phase $\Phi$ of a respiratory cycle of a patient according to a waveform template $\Pi(\Phi)$.

In one form of the present technology, a waveform determination algorithm 4322 may provide a waveform template $\Pi(\Phi)$ with values in the range [0, 1] on the domain of phase values $\Phi$ provided by the phase determination algorithm 4321 to be used by the therapy parameter determination algorithm 4329.

In one form, suitable for either discrete or continuously-valued phase, the waveform template $\Pi(\Phi)$ may be a square-wave template, having a value of 1 for values of phase up to and including 0.5 revolutions, and a value of 0 for values of phase above 0.5 revolutions.

In one form, suitable for continuously-valued phase, the waveform template $\Pi(\Phi)$ may comprise two smoothly curved portions, namely a smoothly curved (e.g., raised cosine) rise from 0 to 1 for values of phase up to 0.5 revolutions, and a smoothly curved (e.g. exponential) decay from 1 to 0 for values of phase above 0.5 revolutions.

In one form, suitable for continuously-valued phase, the waveform template $\Pi(\Phi)$ may be based on a square wave, but with a smooth rise from 0 to 1 for values of phase up to a "rise time" that is less than 0.5 revolutions, and a smooth fall from 1 to 0 for values of phase within a "fall time" after 0.5 revolutions, with a "fall time" that is less than 0.5 revolutions.

In some forms of the present technology, the waveform determination algorithm 4322 may select a waveform template $\Pi(\Phi)$ from a library of waveform templates, dependent on a setting of the RPT device. Each waveform template $\Pi(\Phi)$ in the library may be provided as a lookup table of values $\Pi$ against phase values $\Phi$.

In some forms, the waveform determination algorithm 4322 may compute a waveform template $\Pi(\Phi)$ "on the fly" using a predetermined functional form, possibly parametrised by one or more parameters (e.g., time constant of an exponentially curved portion). The parameters of the functional form may be predetermined or dependent on a current state of the patient 1000.

In some forms of the present technology, suitable for discrete bi-valued phase of either inhalation ($\Phi$=0 revolutions) or exhalation ($\Phi$=0.5 revolutions), the waveform determination algorithm 4322 may compute a waveform template $\Pi$ "on the fly" as a function of both discrete phase $\Phi$ and time t measured since the most recent trigger instant.

In one form, the waveform determination algorithm 4322 may compute the waveform template $\Pi(\Phi, t)$ in two portions (inspiratory and expiratory) as follows:

$$\Pi(\Phi, t) = \begin{cases} \Pi_i(t), & \Phi = 0 \\ \Pi_e(t - T_i), & \Phi = 0.5 \end{cases}$$

where $\Pi_i(t)$ and $\Pi_e(t)$ are inspiratory and expiratory portions of the waveform template $\Pi(\Phi, t)$. In one such form, the inspiratory portion $\Pi_i(t)$ of the waveform template is a smooth rise from 0 to 1 parametrised by a rise time, and the expiratory portion $\Pi_e(t)$ of the waveform template is a smooth fall from 1 to 0 parametrised by a fall time.

5.4.5.2.3 Ventilation Determination

In one form of the present technology, a ventilation determination algorithm 4323 may receive an input a respiratory flow rate Qr, and determine a measure indicative of current patient ventilation, Vent.

In some examples, the ventilation determination algorithm 4323 may determine a measure of ventilation Vent that is an estimate of actual patient ventilation.

One such example is to take half the absolute value of respiratory flow rate, Qr, optionally filtered by low-pass filter such as a second order Bessel low-pass filter with a corner frequency of 0.11 Hz.

In some examples, the ventilation determination algorithm 4323 may determine a measure of ventilation Vent that is broadly proportional to actual patient ventilation.

One such example estimates peak respiratory flow rate Qpeak over the inspiratory portion of the cycle. This and many other procedures involving sampling the respiratory flow rate Qr may produce measures which are broadly proportional to ventilation, provided the flow rate waveform shape does not vary very much (here, the shape of two breaths is taken to be similar when the flow rate waveforms of the breaths normalised in time and amplitude are similar).

In some forms, the ventilation determination algorithm 4323 may determine the median positive respiratory flow rate, the median of the absolute value of respiratory flow rate, and/or the standard deviation of flow rate.

In some forms, arbitrary linear combinations of arbitrary order statistics of the absolute value of respiratory flow rate using positive coefficients, and even some using both positive and negative coefficients, are approximately proportional to ventilation.

In some forms, the ventilation determination algorithm 4323 may determine the mean of the respiratory flow rate in the middle K proportion (by time) of the inspiratory portion, where $0<K<1$. There is an arbitrarily large number of measures that are exactly proportional to ventilation if the flow rate shape is constant.

5.4.5.2.4 Determination of Inspiratory Flow Limitation

In one form of the present technology, the central controller 4230 may execute an inspiratory flow limitation determination algorithm 4324 for the determination of the extent of inspiratory flow limitation.

In one form, the inspiratory flow limitation determination algorithm 4324 may receive as an input a respiratory flow rate signal Qr and provide as an output a metric of the extent to which the inspiratory portion of the breath exhibits inspiratory flow limitation.

In one form of the present technology, the inspiratory portion of each breath may be identified by a zero-crossing detector. A number of evenly spaced points (for example, sixty-five), representing points in time, are interpolated by an interpolator along the inspiratory flow rate-time curve for each breath. The curve described by the points is then scaled by a scalar to have unity length (duration/period) and unity area to remove the effects of changing breathing rate and depth. The scaled breaths are then compared in a comparator with a pre-stored template representing a normal unobstructed breath, similar to the inspiratory portion of the breath. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by the central controller 4230 for the preceding several inspiratory events. This is repeated over the same inspiratory events for the second such point, and so on. Thus, for example, sixty-five scaled data points are generated by the central controller 4230, and represent a moving average of the preceding several inspiratory events, e.g., three events. The moving average of continuously updated values of the (e.g., sixty-five) points are hereinafter called the “scaled flow rate”, designated as Qs(t). Alternatively, a single inspiratory event can be utilised rather than a moving average.

From the scaled flow rate, two shape factors relating to the determination of partial obstruction may be calculated.

Shape factor 1 is the ratio of the mean of the middle (e.g., thirty-two) scaled flow rate points to the mean overall (e.g. sixty-five) scaled flow rate points. Where this ratio is in excess of unity, the breath will be taken to be normal. Where the ratio is unity or less, the breath will be taken to be obstructed. A ratio of about 1.17 is taken as a threshold between partially obstructed and unobstructed breathing and equates to a degree of obstruction that would permit maintenance of adequate oxygenation in a typical patient.

Shape factor 2 is calculated as the RMS deviation from unit scaled flow rate, taken over the middle (e.g., thirty-two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can be other than those described.

5.4.5.2.5 Determination of Apneas and Hypopneas

In one form of the present technology, the central controller 4230 may execute an apnea/hypopnea determination algorithm 4325 for the determination of the presence of apneas and/or hypopneas.

In one form, the apnea/hypopnea determination algorithm 4325 may receive as an input a respiratory flow rate signal Qr and provide as an output a flag that indicates that an apnea or a hypopnea has been detected.

In one form, an apnea may be said to have been detected when a function of respiratory flow rate Qr falls below a flow rate threshold for a predetermined period of time. The function may determine a peak flow rate, a relatively short-term mean flow rate, and/or a flow rate intermediate of relatively short-term mean and peak flow rate, for example an RMS flow rate. The flow rate threshold may be a relatively long-term measure of flow rate.

In one form, a hypopnea may be said to have been detected when a function of respiratory flow rate Qr falls below a second flow rate threshold for a predetermined period of time. The function may determine a peak flow, a relatively short-term mean flow rate, and/or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

5.4.5.2.6 Determination of Snore

In one form of the present technology, the central controller 4230 may execute one or more snore determination algorithms 4326 for the determination of the extent of snore.

In one form, the snore determination algorithm 4326 may receive as an input a respiratory flow rate signal Qr and provide as an output a metric of the extent to which snoring is present.

The snore determination algorithm 4326 may comprise the step of determining the intensity of the flow rate signal in the range of 30-300 Hz. Further, the snore determination algorithm 4326 may comprise a step of filtering the respiratory flow rate signal Qr to reduce background noise, e.g., the sound of airflow in the system from the blower.

5.4.5.2.7 Determination of Airway Patency

In one form of the present technology, the central controller 4230 may execute one or more airway patency determination algorithms 4327 for the determination of the extent of airway patency.

In one form, the airway patency determination algorithm 4327 may receive as an input a respiratory flow rate signal Qr, and determine the power of the signal in the frequency range of about 0.75 Hz and about 3 Hz. The presence of a peak in this frequency range may be taken to indicate an open airway. The absence of a peak may be taken to be an indication of a closed airway.

In one form, the frequency range within which the peak is sought is the frequency of a small forced oscillation in the treatment pressure Pt. In one example, the forced oscillation is of frequency 2 Hz with amplitude about 1 $cmH_2O$.

In one form, airway patency determination algorithm 4327 may receive as an input a respiratory flow rate signal Qr, and determine the presence or absence of a cardiogenic signal. The absence of a cardiogenic signal may be taken to be an indication of a closed airway.

5.4.5.2.8 Determination of Target Ventilation

In one form of the present technology, the central controller 4230 may take as input the measure of current ventilation, Vent, and execute one or more target ventilation determination algorithms 4328 for the determination of a target value Vtgt for the measure of ventilation.

In some forms of the present technology, there may be no target ventilation determination algorithm 4328, and the target value Vtgt is predetermined.

In one form, the target value Vtgt may be predetermined by hard-coding during configuration of the RPT device 4000.

In one form, the target value Vtgt may be predetermined by manual entry through the input device 4220.

In some forms of the present technology, such as adaptive servo-ventilation (ASV), the target ventilation determination algorithm 4328 may compute a target value Vtgt from a value Vtyp indicative of the typical recent ventilation of the patient.

In some forms of adaptive servo-ventilation, the target ventilation Vtgt may be computed as a high proportion of, but less than, the typical recent ventilation Vtyp. The high proportion in such forms may be in the range (80%, 100%), or (85%, 95%), or (87%, 92%).

In some forms of adaptive servo-ventilation, the target ventilation Vtgt may be computed as a slightly greater than unity multiple of the typical recent ventilation Vtyp.

The typical recent ventilation Vtyp may be the value around which the distribution of the measure of current ventilation Vent over multiple time instants over some predetermined timescale tends to cluster, that is, a measure of the central tendency of the measure of current ventilation over recent history.

In one example of the target ventilation determination algorithm 4328, the recent history is of the order of several minutes, but in any case, should be longer than the timescale of Cheyne-Stokes waxing and waning cycles. The target ventilation determination algorithm 4328 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

5.4.5.2.9 Determination of Therapy Parameters

In some forms of the present technology, the central controller 4230 may execute one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt using the equation $$Pt=A\Pi(\Phi,t)+P_0 \quad (1)$$

where:

A is the amplitude, $\Pi(\Phi, t)$ is the waveform template value (in the range 0 to 1) at the current value $\Phi$ of phase and t of time, and $P_0$ is a base pressure.

If the waveform determination algorithm 4322 provides the waveform template $\Pi(\Phi, t)$ as a lookup table of values $\Pi$ indexed by phase $\Phi$, the therapy parameter determination algorithm 4329 applies equation (1) by locating the nearest lookup table entry to the current value $\Phi$ of phase returned by the phase determination algorithm 4321, or by interpolation between the two entries straddling the current value $\Phi$ of phase.

The values of the amplitude A and the base pressure $P_0$ may be set by the therapy parameter determination algorithm 4329 depending on the chosen respiratory pressure therapy mode in the manner described below.

5.4.5.3 Therapy Control Module

The therapy control module 4330 in accordance with one aspect of the present technology may receive as inputs the therapy parameters from the therapy parameter determination algorithm 4329 of the therapy engine module 4320, and control the pressure generator 4140 to deliver a flow of air in accordance with the therapy parameters.

In one form of the present technology, the therapy parameter may be a treatment pressure Pt, and the therapy control module 4330 may control the pressure generator 4140 to deliver a flow of air whose interface pressure Pm at the patient interface 3000 is equal to the treatment pressure Pt.

5.4.5.4 Detection of Fault Conditions

In one form of the present technology, the central controller 4230 may execute one or more methods 4340 for the detection of fault conditions. The fault conditions detected by the one or more methods 4340 may include at least one of the following:

- Power failure (no power, or insufficient power)
- Transducer fault detection
- Failure to detect the presence of a component
- Operating parameters outside recommended ranges (e.g., pressure, flow rate, temperature, PaO2)
- Failure of a test alarm to generate a detectable alarm signal.

Upon detection of the fault condition, the corresponding method 4340 may signal the presence of the fault by one or more of the following:

- Initiation of an audible, visual &/or kinetic (e.g., vibrating) alarm
- Sending a message to an external device
- Logging of the incident 5.5 Air Circuit An air circuit 4170 in accordance with an aspect of the present technology may be a conduit or a tube constructed and arranged to allow, in use, a flow of air to travel between two components such as RPT device 4000 and the patient interface 3000.

5.6 Respiratory Therapy Modes

Various respiratory therapy modes may be implemented by the disclosed respiratory therapy system.

5.6.1 CPAP Therapy

In some examples of respiratory pressure therapy, the central controller 4230 may set the treatment pressure Pt according to the treatment pressure equation (1) as part of the therapy parameter determination algorithm 4329.

In one example, the amplitude A may be identically zero, so the treatment pressure Pt (which represents a target value to be achieved by the interface pressure Pm at the current instant of time) is identically equal to the base pressure $P_o$ throughout the respiratory cycle. Such an example may be generally grouped under the heading of CPAP therapy. In such examples, there is no need for the therapy engine module 4320 to determine phase Φ or the waveform template Π(Φ).

In some forms of CPAP therapy, the base pressure $P_0$ may be a constant value that is hard-coded or manually entered to the RPT device 4000.

In some forms, the central controller 4230 may repeatedly compute the base pressure $P_0$ as a function of indices or measures of sleep disordered breathing returned by the respective algorithms in the therapy engine module 4320, such as one or more of flow limitation, apnea, hypopnea, patency, and snore. Such form may be sometimes referred to as APAP therapy.

Figure 3E:
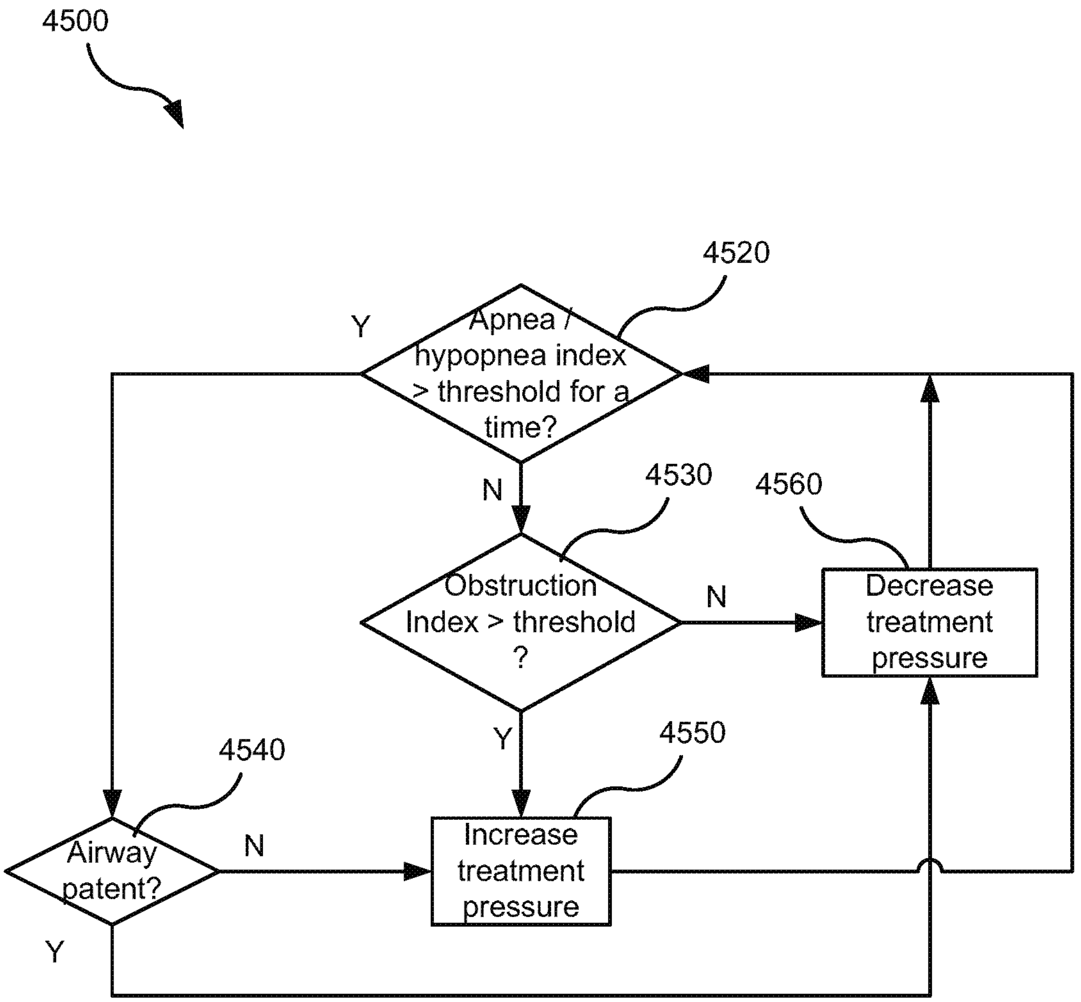

FIG. 3E is a flow chart illustrating a method 4500 carried out by the central controller 4230 to continuously compute the base pressure $P_0$ as part of an APAP therapy implementation of the therapy parameter determination algorithm 4329, when the pressure support A is identically zero.

The method 4500 starts at step 4520, at which the central controller 4230 compares the measure of the presence of apnea/hypopnea with a first threshold and determines whether the measure of the presence of apnea/hypopnea has exceeded the first threshold for a predetermined period of time, indicating an apnea/hypopnea is occurring. If so, the method 4500 proceeds to step 4540; otherwise, the method 4500 proceeds to step 4530. At step 4540, the central controller 4230 compares the measure of airway patency with a second threshold. If the measure of airway patency exceeds the second threshold, indicating the airway is patent, the detected apnea/hypopnea is deemed central, and the method 4500 proceeds to step 4560; otherwise, the apnea/hypopnea is deemed obstructive, and the method 4500 proceeds to step 4550.

At step 4530, the central controller 4230 compares the measure of flow limitation with a third threshold. If the measure of flow limitation exceeds the third threshold, indicating inspiratory flow is limited, the method 4500 proceeds to step 4550; otherwise, the method 4500 proceeds to step 4560.

At step 4550, the central controller 4230 increases the base pressure $P_0$ by a predetermined pressure increment $\Delta P$, provided the resulting treatment pressure Pt would not exceed a maximum treatment pressure Pmax. In one implementation, the predetermined pressure increment $\Delta P$ and maximum treatment pressure Pmax are 1 cmH2O and 25 cmH2O respectively. In other implementations, the pressure increment $\Delta P$ can be as low as 0.1 cmH2O and as high as 3 cmH2O, or as low as 0.5 cmH2O and as high as 2 cmH2O. In other implementations, the maximum treatment pressure Pmax can be as low as 15 cmH2O and as high as 35 cmH2O, or as low as 20 cmH2O and as high as 30 cmH2O. The method 4500 then returns to step 4520.

At step 4560, the central controller 4230 decreases the base pressure $P_0$ by a decrement, provided the decreased base pressure $P_0$ would not fall below a minimum treatment pressure Pmin. The method 4500 then returns to step 4520. In one implementation, the decrement is proportional to the value of $P_0$-Pmin, so that the decrease in $P_0$ to the minimum treatment pressure Pmin in the absence of any detected events is exponential. In one implementation, the constant of proportionality is set such that the time constant τ of the exponential decrease of $P_0$ is 60 minutes, and the minimum treatment pressure Pmin is 4 cmH2O. In other implementations, the time constant τ could be as low as 1 minute and as high as 300 minutes, or as low as 5 minutes and as high as 180 minutes. In other implementations, the minimum treatment pressure Pmin can be as low as 0 cmH2O and as high as 8 cmH2O, or as low as 2 cmH2O and as high as 6 cmH2O. Alternatively, the decrement in $P_0$ could be predetermined, so the decrease in $P_0$ to the minimum treatment pressure Pmin in the absence of any detected events is linear.

5.6.2 Bi-Level Therapy

In some examples of the present technology, the value of amplitude A in equation (1) may be positive. Such examples may be known as bi-level therapy, because in determining the treatment pressure Pt using equation (1) with positive amplitude A, the therapy parameter determination algorithm 4329 oscillates the treatment pressure Pt between two values or levels in synchrony with the spontaneous respiratory effort of the patient 1000. That is, based on the typical waveform templates Π(Φ, t) described above, the therapy parameter determination algorithm 4329 increases the treatment pressure Pt to $P_0$+A (known as the IPAP) at the start of, or during, or inspiration and decreases the treatment pressure Pt to the base pressure $P_0$ (known as the EPAP) at the start of, or during, expiration.

In some forms of bi-level therapy, the IPAP may be a treatment pressure that has the same purpose as the treatment pressure in CPAP therapy modes, and the EPAP is the IPAP minus the amplitude A, which has a "small" value (a few cmH2O) sometimes referred to as the Expiratory Pressure Relief (EPR). Such forms may be referred to as CPAP therapy with EPR, which is generally thought to be more comfortable than straight CPAP therapy.

In some examples of CPAP therapy with EPR, either or both of the IPAP and the EPAP may be constant values that are hard-coded or manually entered to the RPT device 4000.

In some forms of CPAP therapy with EPR, the therapy parameter determination algorithm 4329 may repeatedly compute the IPAP and/or the EPAP during CPAP with EPR. In one form, the therapy parameter determination algorithm 4329 repeatedly computes the EPAP and/or the IPAP as a function of indices or measures of sleep disordered breathing returned by the respective algorithms in the therapy engine module 4320 in analogous fashion to the computation of the base pressure $P_0$ in APAP therapy described above.

In some forms of bi-level therapy, the amplitude A is large enough that the RPT device 4000 may do some or all of the work of breathing of the patient 1000. In such forms, known as pressure support ventilation therapy, the amplitude A may be referred to as the pressure support, or swing. In pressure support ventilation therapy, the IPAP is the base pressure $P_0$ plus the pressure support A, and the EPAP is the base pressure $P_0$.

In some forms of pressure support ventilation therapy, known as fixed pressure support ventilation therapy, the pressure support A may be fixed at a predetermined value, e.g., 10 cmH2O. The predetermined pressure support value is a setting of the RPT device 4000 and may be set for example by hard-coding during configuration of the RPT device 4000 or by manual entry through the input device 4220.

In other forms of pressure support ventilation therapy, broadly known as servo-ventilation, the therapy parameter determination algorithm 4329 may take as input some currently measured or estimated parameter of the respiratory cycle (e.g. the current measure Vent of ventilation) and a target value of that respiratory parameter (e.g. a target value Vtgt of ventilation) and repeatedly adjust the parameters of equation (1) to bring the current measure of the respiratory parameter towards the target value.

In one form of servo-ventilation, known as adaptive servo-ventilation (ASV), which has been used to treat CSR, the respiratory parameter may be ventilation, and the target ventilation value Vtgt may be computed by the target ventilation determination algorithm 4328 from the typical recent ventilation Vtyp, as described above.

In some forms of servo-ventilation, the therapy parameter determination algorithm 4329 may apply a control methodology to repeatedly compute the pressure support A so as to bring the current measure of the respiratory parameter towards the target value.

In one form, the control methodology may be Proportional-Integral (PI) control.

In one example of PI control, suitable for ASV modes in which a target ventilation Vtgt is set to slightly less than the typical recent ventilation Vtyp, the pressure support A may be repeatedly computed as:

$$A=G\int(\text{Vent}-\text{Vtgt})dt \quad (2)$$

where G is the gain of the PI control. Larger values of gain G can result in positive feedback in the therapy engine module 4320. Smaller values of gain G may permit some residual untreated CSR or central sleep apnea.

In some examples, the gain G is fixed at a predetermined value, such as −0.4 cmH2O/(L/min)/sec.

In some examples, the gain G may be varied between therapy sessions, starting small and increasing from session to session until a value that substantially eliminates CSR is reached.

In some forms, conventional means for retrospectively analysing the parameters of a therapy session to assess the severity of CSR during the therapy session may be employed in such implementations.

In some forms, the gain G may vary depending on the difference between the current measure Vent of ventilation and the target ventilation Vtgt.

In some examples, the servo-ventilation control methodologies that may be applied by the therapy parameter determination algorithm 4329 include proportional (P), proportional-differential (PD), and proportional-integral-differential (PID).

In one example, the value of the pressure support A computed via equation (2) may be clipped to a range defined as [Amin, Amax]. Thus, the pressure support A sits by default at the minimum pressure support Amin until the measure of current ventilation Vent falls below the target ventilation Vtgt, at which point A starts increasing, only falling back to Amin when Vent exceeds Vtgt once again.

The pressure support limits Amin and Amax may be settings of the RPT device 4000, set for example by hard-coding during configuration of the RPT device 4000 or by manual entry through the input device 4220.

In pressure support ventilation therapy modes, the EPAP is the base pressure $P_0$. As with the base pressure $P_0$ in CPAP therapy, the EPAP may be a constant value that is prescribed or determined during titration. Titration of the EPAP for a given patient may be performed by a clinician during a titration session with the aid of PSG, with the aim of preventing obstructive apneas, thereby maintaining an open airway for the pressure support ventilation therapy, in similar fashion to titration of the base pressure $P_0$ in constant CPAP therapy. This alternative is sometimes referred to as fixed-EPAP pressure support ventilation therapy.

In one form, a constant EPAP may be set for example by hard-coding during configuration of the RPT device 4000 or by manual entry through the input device 4220.

In one form, the therapy parameter determination algorithm 4329 may repeatedly compute the base pressure $P_0$ during pressure support ventilation therapy. The therapy parameter determination algorithm 4329 may repeatedly compute the EPAP as a function of indices or measures of sleep disordered breathing returned by the respective algorithms in the therapy engine module 4320, such as one or more of flow limitation, apnea, hypopnea, patency, and snore. Because the continuous computation of the EPAP resembles the manual adjustment of the EPAP by a clinician during titration of the EPAP, this process is also sometimes referred to as auto-titration of the EPAP, and the therapy mode may be known as auto-titrating EPAP pressure support ventilation therapy, or auto-EPAP pressure support ventilation therapy.

5.6.3 High Flow Therapy

In other forms of respiratory therapy, the pressure of the flow of air may not be controlled as it is for respiratory pressure therapy. For example, the central controller 4230 may control the pressure generator 4140 to deliver a flow of air whose device flow rate Qd is controlled to a treatment or target flow rate Qtgt that is typically positive throughout the patient's breathing cycle. Such forms are generally grouped under the heading of flow therapy.

In some forms of flow therapy, the treatment flow rate Qtgt may be a constant value that is hard-coded or manually entered to the RPT device 4000. If the treatment flow rate Qtgt is sufficient to exceed the patient's peak inspiratory flow rate, the therapy is generally referred to as high flow therapy (HFT).

In some forms of flow therapy, the treatment flow rate may be a profile Qtgt(t) that varies over the respiratory cycle.

5.7 Glossary

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g., oxygen enriched air.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g., the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g., from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Oxygen enriched air: Air with a concentration of oxygen greater than that of atmospheric air (21%), for example at least about 50% oxygen, at least about 60% oxygen, at least about 70% oxygen, at least about 80% oxygen, at least about 90% oxygen, at least about 95% oxygen, at least about 98% oxygen, or at least about 99% oxygen. "Oxygen enriched air" is sometimes shortened to "oxygen".

Medical Oxygen: Medical oxygen is defined as oxygen enriched air with an oxygen concentration of 80% or greater.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal (1 hectopascal=100 Pa=100 N/$m^2$=1 millibar~0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

5.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.7.1.2 Mechanical Properties

Resilience: Ability of a material to absorb energy when deformed elastically and to release the energy upon unloading.

Resilient: Will release substantially all of the energy when unloaded. Includes e.g., certain silicones, and thermoplastic elastomers.

Hardness: The ability of a material per se to resist deformation (e.g., described by a Young's Modulus, or an indentation hardness scale measured on a standardised sample size).

'Soft' materials may include silicone or thermo-plastic elastomer (TPE), and may, e.g., readily deform under finger pressure.

'Hard' materials may include polycarbonate, polypropylene, steel or aluminium, and may not e.g., readily deform under finger pressure.

Stiffness (or rigidity) of a structure or component: The ability of the structure or component to resist deformation in response to an applied load. The load may be a force or a moment, e.g., compression, tension, bending or torsion. The structure or component may offer different resistances in different directions. The inverse of stiffness is flexibility.

Floppy structure or component: A structure or component that will change shape, e.g., bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g., at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.7.2 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g., about 360 degrees. In certain forms an elbow may be removable from a mating component, e.g., via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Functional dead space: (description to be inserted here)

Headgear: Headgear will be taken to mean a form of positioning and stabilizing structure designed for use on a head. For example, the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms “a”, “an”, and “the” include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms “comprises” and “comprising” should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms “first” and “second” may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

The invention claimed is:

1. An apparatus for providing positive pressure respiratory therapy to a patient breathing in a respiratory cycle including an inhalation portion and an exhalation portion, said apparatus comprising:

a controllable motor-blower configured to generate a supply of air at a positive pressure relative to ambient pressure;

a controller configured to adjust operation of said motor-blower;

a housing holding said motor-blower, the housing including an anchor configured to secure a patient interface to the apparatus when not in use by the patient; and at least one sensor associated with the anchor, wherein the controller is configured to cut power to the controllable motor-blower on determining, via signal from the at least one sensor, that the patient interface is secured to the anchor.

2. The apparatus according to claim 1, wherein the anchor is removable from the housing.

3. The apparatus according to claim 1, wherein the anchor is positioned on an external surface of the housing or within the housing.

4. The apparatus according to claim 1, wherein the anchor is magnetic.

5. The apparatus according to claim 4, wherein the controller determines via the at least one sensor whether the patient interface is secured to the anchor based on changes in a magnetic field.

6. The apparatus according to claim 1, wherein the anchor is configured to provide a clearance between the patient interface and the housing when the patient interface is secured to the housing.

7. The apparatus according to claim 1, wherein the anchor includes a tie, a press stud, a strap, a hook and/or loop fastener, an adhesive, an interlocking mechanism, a reclosable fastener, an electrostatic fastener, or any combination of thereof.

8. The apparatus according to claim 1, further comprising a humidifier, the anchor being positioned so as to not hinder a user from removing the humidifier from the apparatus.

9. An apparatus for providing positive pressure respiratory therapy to a patient breathing in a respiratory cycle including an inhalation portion and an exhalation portion, said apparatus comprising:

a controllable motor-blower configured to generate a supply of air at a positive pressure relative to ambient pressure;

a controller configured to adjust operation of said motor-blower; and a housing holding said motor-blower, the housing including an anchor configured to secure a patient interface to the apparatus when not in use by the patient, wherein the anchor is configured to secure the patient interface in a contactless manner.

10. The apparatus according to claim 1, wherein the anchor comprises a connector for electrical communication between the patient interface and the apparatus.

11. The apparatus according to claim 1, wherein the anchor comprises a charger.

12. The apparatus according to claim 11, wherein the charger is an inductive charger, a resonant inductive charger and/or a radio frequency based charger.

13. An apparatus for providing positive pressure respiratory therapy to a patient breathing in a respiratory cycle including an inhalation portion and an exhalation portion, said apparatus comprising:

a controllable motor-blower configured to generate a supply of air at a positive pressure relative to ambient pressure;

a controller configured to adjust operation of said motor-blower;

a housing holding said motor-blower, the housing including an anchor configured to secure a patient interface to the apparatus when not in use by the patient, wherein the controller is configured to supply power to the controllable motor-blower on determining, via at least one sensor, that the patient interface is not secured to the anchor.

14. The apparatus according to claim 1, wherein the controller determines via the at least one sensor whether the patient interface is secured to the anchor based on an electrical current flowing through the anchor.

15. A system comprising an apparatus for providing positive pressure respiratory therapy to a patient breathing in a respiratory cycle including an inhalation portion and an exhalation portion according to claim 1, and the patient interface having a complementary structure that engages the anchor of the apparatus.

16. The system according to claim 15, wherein the complementary structure is defined by the patient interface.

17. The system according to claim 15, wherein the patient interface includes a flat surface and the complementary structure is defined by or provided on said flat surface.

18. The system according to claim 15, wherein the complementary structure is an attachment or accessory provided to the patient interface.

19. The system according to claim 15, wherein the complementary structure includes a tie, a clip, a press stud, a strap, and/or a hook and/or loop fastener.

20. The system according to claim 15, wherein the complementary structure is magnetic.

21. The system according to claim 15, wherein the complementary structure is removable from the patient interface.

22. The system according to claim 15, wherein the patient interface is structured to be oriented in an upright position when the anchor and the complementary structure are engaged.

* * * * *